US011446161B2

(12) United States Patent
Rogers et al.

(10) Patent No.: US 11,446,161 B2
(45) Date of Patent: Sep. 20, 2022

(54) TRANSLATING DUAL AXIS ADJUSTABLE INTERBODY FUSION SPINAL SYSTEM

(71) Applicant: SpineEX, Inc., Fremont, CA (US)

(72) Inventors: Andrew Rogers, Deephaven, MN (US); Robyn Burrows-Ownbey, Elmdale, KS (US); Eric Blossey, Denver, CO (US)

(73) Assignee: Adcura, Inc., Eden Prairie, MN (US)

( * ) Notice: Subject to any disclaimer, the term of this patent is extended or adjusted under 35 U.S.C. 154(b) by 61 days.

(21) Appl. No.: 16/993,264

(22) Filed: Aug. 14, 2020

(65) Prior Publication Data

US 2021/0045891 A1 Feb. 18, 2021

Related U.S. Application Data

(60) Provisional application No. 62/887,188, filed on Aug. 15, 2019.

(51) Int. Cl.
*A61F 2/44* (2006.01)
*A61F 2/30* (2006.01)

(52) U.S. Cl.
CPC ............ *A61F 2/447* (2013.01); *A61F 2/4425* (2013.01); *A61F 2002/30405* (2013.01); *A61F 2002/30476* (2013.01); *A61F 2002/443* (2013.01)

(58) Field of Classification Search
CPC .............................. A61F 2/4455–2/447; A61F 2002/30523–2002/30525; A61F 2002/30545; A61F 2002/30553–2002/30556; A61F 2002/30579
See application file for complete search history.

(56) References Cited

U.S. PATENT DOCUMENTS

| | | |
|---|---|---|
| 5,171,278 A | 12/1992 | Pisharodi |
| 5,653,763 A | 8/1997 | Eerrico |
| 5,665,122 A | 9/1997 | Kambin |
| 5,693,100 A | 12/1997 | Pisharodi |
| 6,129,763 A | 10/2000 | Chauvin |
| 6,159,244 A | 12/2000 | Suddaby |
| 6,174,334 B1 | 1/2001 | Suddaby |
| 6,193,757 B1 | 2/2001 | Foley |
| 6,436,140 B1 | 8/2002 | Liu |
| 6,641,614 B1 | 11/2003 | Wagner |
| 6,905,512 B2 | 6/2005 | Paes |
| 7,094,257 B2 | 8/2006 | Mujwid |

(Continued)

FOREIGN PATENT DOCUMENTS

| | | |
|---|---|---|
| CN | 201861800 | 6/2011 |
| CN | 102369332 | 3/2012 |

(Continued)

OTHER PUBLICATIONS

PCT, International Search Report and Written Opinion of International Searching Authority in PCT/US2020/046258, dated Dec. 10, 2020, 7 pages.

(Continued)

*Primary Examiner* — Julianna N Harvey
(74) *Attorney, Agent, or Firm* — Adcura IP

(57) ABSTRACT

An interbody fusion device employs a torque transfer mechanism to transfer torque to a driving mechanism responsible for expansion of the interbody fusion device in a direction non-parallel to a longitudinal axis of the driving mechanism.

24 Claims, 16 Drawing Sheets

(56) References Cited

U.S. PATENT DOCUMENTS

| | | |
|---|---|---|
| 7,569,074 B2 | 8/2009 | Eisermann |
| 7,674,296 B2 | 3/2010 | Rhoda |
| 7,708,778 B2 | 5/2010 | Gordon |
| 7,753,958 B2 | 7/2010 | Gordon |
| D626,233 S | 10/2010 | Cipoletti |
| 8,062,375 B2 | 11/2011 | Glerum |
| 8,192,495 B2 | 6/2012 | Simpson |
| 8,221,501 B2 | 7/2012 | Eisermann |
| 8,303,663 B2 | 11/2012 | Jimenez |
| 8,394,143 B2 | 3/2013 | Grotz |
| 8,398,713 B2 | 3/2013 | Weiman |
| 2002/0151977 A1 | 10/2002 | Paes |
| 2002/0161444 A1 | 10/2002 | Choi |
| 2004/0088054 A1* | 5/2004 | Berry ............... A61F 2/4455 623/17.11 |
| 2005/0010295 A1 | 1/2005 | Michelson |
| 2005/0256576 A1* | 11/2005 | Moskowitz ......... A61F 2/441 606/104 |
| 2005/0283244 A1 | 12/2005 | Gordon |
| 2005/0283245 A1 | 12/2005 | Gordon |
| 2006/0129244 A1 | 6/2006 | Ensign |
| 2006/0149385 A1* | 7/2006 | McKay ............. A61F 2/4455 623/17.15 |
| 2006/0206207 A1 | 9/2006 | Dryer |
| 2007/0100340 A1 | 5/2007 | Lange et al. |
| 2008/0147194 A1 | 6/2008 | Grotz |
| 2008/0300598 A1 | 12/2008 | Barreiro |
| 2009/0210062 A1 | 8/2009 | Thalgott |
| 2009/0222100 A1 | 9/2009 | Cipoletti |
| 2010/0082109 A1 | 4/2010 | Greenhalgh |
| 2010/0185291 A1 | 7/2010 | Jimenez |
| 2011/0035011 A1 | 2/2011 | Cain |
| 2012/0290097 A1 | 11/2012 | Cipoletti |
| 2012/0323327 A1 | 12/2012 | McAfee |
| 2013/0053966 A1 | 2/2013 | Jimenez |
| 2013/0158668 A1* | 6/2013 | Nichols ............. A61F 2/4611 623/17.16 |
| 2013/0253650 A1* | 9/2013 | Ashley ............. A61F 2/4465 623/17.16 |
| 2014/0288652 A1 | 9/2014 | Boehm et al. |
| 2015/0018957 A1* | 1/2015 | Nichols ............... A61F 2/44 623/17.16 |
| 2015/0066145 A1* | 3/2015 | Rogers ............. A61F 2/4611 623/17.15 |
| 2015/0351925 A1* | 12/2015 | Emerick ........... A61F 2/4611 29/11 |
| 2017/0119542 A1* | 5/2017 | Logan ............. A61F 2/4465 |
| 2017/0209282 A1* | 7/2017 | Aghayev .......... A61F 2/4455 |
| 2018/0360616 A1* | 12/2018 | Luu ................. A61F 2/447 |
| 2019/0070015 A1* | 3/2019 | Emerick ........... A61F 2/442 |
| 2019/0336302 A1* | 11/2019 | Seifert ............. A61F 2/4425 |

FOREIGN PATENT DOCUMENTS

| | | |
|---|---|---|
| EP | 1925272 | 1/2010 |
| EP | 1706075 | 1/2011 |
| EP | 1903994 | 6/2011 |
| WO | 2005058209 | 6/2005 |
| WO | 2009124269 | 10/2009 |
| WO | 2012112596 | 8/2012 |

OTHER PUBLICATIONS

PCT, International Search Report and Written Opinion of International Searching Authority in PCT/US2014/53551, dated Dec. 18, 2014, 12 pages.

EPO, Office Action and Written Opinion in EP 14841270.3, dated Apr. 20, 2017, 5 pages.

Japanese Patent Office, Office Action in Japanese Application No. 2016-537917, dated Jun. 4, 2018, 9 pages.

* cited by examiner

TRANSLATING DUAL AXIS ADJUSTABLE INTERBODY FUSION SPINAL SYSTEM

TECHNICAL FIELD

This disclosure relates in general to apparatuses, systems, and methods for treating spinal diseases. In particular, various embodiments of expandable and adjustable lordosis interbody fusion devices are described.

BACKGROUND

Spinal fusion is a surgical procedure to correct problems relating to the human spine such as degenerative disc disease (DDD), spondylolisthesis, recurrent disc herniation, etc. It generally involves removing damaged disc and bone from between adjacent vertebrae and inserting bone graft material that promotes bone growth. As the bone grows, the adjacent vertebrae join, or fuse, together. Fusing the bones together can help make that particular area of the spine more stable and help reduce problems related to nerve irritation at the site of the fusion. Fusions can be done at one or more segments of the spine.

In an interbody spinal fusion procedure, the nucleus pulposus and/or the annulus fibrosus that compose the intervertebral disc at the point of the damage are removed and an implant configured in shape and dimension is placed in the disc space to restore the distance between adjacent vertebrae to a proper condition. Surgical approaches to implement interbody fusion vary, and access to the patient's vertebral column can be made through the abdomen or back. One surgical method for accomplishing lumbar spinal fusion in a less invasive way involves accessing the vertebral column through a small incision on the posterior side where the surgeon removes a portion of bone and joint at the back and side of the vertebrae. These sections of bone and joint are called, respectively, the lamina and the facet joint. This procedure is known as transforaminal lumbar interbody fusion (TLIF). The transforaminal technique allows the surgeon to insert bone graft and spacer into the disc space from a unilateral approach laterally without having to forcefully retract the nerve roots, which can reduce injury and scarring around the nerve roots as compared to the more traditional posterior lumbar interbody fusion procedure (PLIF), which requires nerve root retraction and a bilateral approach. Other common surgical methods or approaches for reaching the desired intervertebral disc of concern are through access of the anterior and/or anterolateral column of the spine. Lateral lumbar interbody fusion (LLIF) is a minimally invasive procedure in which the surgeon accesses the spine through a small surgical incision in the side with dissection of the psoas muscle or navigation around the psoas muscle, also known as anterior-to-psoas lateral lumbar interbody fusion (ATP LLIF). LLIF and ATP LLIF procedures allow for delivery of larger interbody fusion device footprints with minimal disruption of the patient's anatomy, along with the ability to perform indirect decompression of the nerve root elements. Anterior Lumbar Interbody Fusion (ALIF) is a procedure in which the surgeon accesses the desired intervertebral disc of concern through an open incision in the abdomen navigating through the abdominal muscles as well as bypassing organs and vascular structures. ALIF procedures allow for delivery of larger interbody fusion devices in comparison to any other interbody fusion procedure, which in turn provide good indirect decompression and risk against subsidence or sinking of the delivered implant into the vertebral body elements.

Conventionally, once the intervertebral disc is removed from the body, the surgeon typically forces different trial implants between the vertebral bodies of the specific region to determine the size of the implant for maintaining a proper distance between the adjacent vertebrae. A proper angle between the vertebral bodies also must be maintained to accommodate the natural curvature of the spine e.g. the lordosis. Therefore, during selection of a fusion device for implantation, both intervertebral disc height and lordosis must be considered. Traditional implant devices are often pre-configured to have top and bottom surface angles to accommodate the natural curvature of the spine. It is unlikely or difficult that these values can be determined precisely prior to the operation. Further, in implementing a trial-and-error approach to sizing and fitting the interbody fusion device into the target region for geometric configuration, the patient is subjected to significant invasive activity. If a hyperlordotic sagittal profile configuration ($\geq 20°$) is set or supplemental fixation for the lumbosacral levels is desired, the surgeon may place a spinal construct in the form of anterior column fixation such as an additional plate and screw assembly to prevent possible movement or migration of the fusion device in the intervertebral disc space and/or to provide temporary stabilization of the anterior column of the spine during the spinal fusion process until arthrodesis takes place. This can require the surgeon to perform a secondary surgery after placing the fusion device, which in turn would lengthen the overall surgery time leading to more potential blood loss and complications with anesthesia for the patient.

SUMMARY

An example interbody fusion device comprises a housing, a driving mechanism operable to expand and/or contract the housing, and a gear assembly operable to transfer torque to the driving mechanism. The driving mechanism comprise an axle having a longitudinal axis. The gear assembly comprises a first translating gear coupled to the axle and a first driving gear configured to receive torque applied from a direction non-parallel to the longitudinal axis of the axle and drive the first translating gear, whereby application of torque to the first driving gear causes the first translating gear and the axle to rotate about the longitudinal axis, thereby actuating the driving mechanism to effect expansion and/or contraction of the housing.

An example interbody fusion device comprises a housing, a first driving mechanism, a second driving mechanism, a first gear assembly, and a second gear assembly. The first driving mechanism is arranged in the housing at a first lateral area. The second driving mechanism is arranged in the housing at a second lateral area. The first driving mechanism comprises a first axle having a longitudinal axis. The second driving mechanism comprises a second axle having a longitudinal axis. The first gear assembly is operable to transmit torque to the first driving mechanism. The first gear assembly comprise a translating gear coupled to the first axle and a driving gear configured to receive torque applied from a direction non-parallel to the longitudinal axis of the first axle and drive the translating gear, whereby application of torque to the driving gear causes the translating gear and the first axle to rotate about the longitudinal axis of the first axle, thereby actuating the first driving mechanism to effect expansion and/or contraction of the housing at the first lateral area. The second gear assembly is operable to transmit torque to the second driving mechanism. The second gear assembly comprises a first translating gear coupled to the second axle and a first driving gear configured to receive torque applied from a direction non-parallel to the longitudinal axis of the second axle and drive the first translating gear, whereby application of torque to the first driving gear causes the first translating gear and the second axle to rotate about the longitudinal axis of the second axle, thereby actuating the second driving mechanism to effect expansion and/or contraction of the housing at the second lateral area.

This Summary is provided to introduce selected embodiments in a simplified form and is not intended to identify key features or essential characteristics of the claimed subject matter, nor is it intended to be used as an aid in determining the scope of the claimed subject matter. The selected embodiments are presented merely to provide the reader with a brief summary of certain forms the invention might take and are not intended to limit the scope of the invention. Other aspects and embodiments of the disclosure are described in the section of Detailed Description.

BRIEF DESCRIPTION OF THE DRAWINGS

These and various other features and advantages of the disclosure will become better understood upon reading of the following detailed description and the appended claims in conjunction with the accompanying drawings, where:

FIG. 1A is an isometric view, FIG. 1B a top view, FIG. 1C a partially exploded view, and FIG. 1D a cross-sectional view.

FIG. 2A is a perspective view, FIG. 2B a close-up perspective view, and FIG. 2C is a close-up side view.

FIG. 3A is a cross-sectional view emphasizing a first driver and a second driver of a surgical instrument, FIG. 3B a cross-sectional view showing engagement of an interbody fusion device with a surgical instrument in an expansion mode (simultaneous dual-axis adjustment), FIG. 3C a cross-sectional view showing engagement of an interbody fusion device with a surgical instrument in a lordosis mode (independent anterior axis adjustment), and FIG. 3D a cross-sectional view showing engagement of an interbody fusion device with a surgical instrument in another lordosis mode (independent posterior axis adjustment).

FIG. 9A is an anterior view, and FIG. 9B a lateral view.

FIG. 10A is an exploded view, and FIG. 10B an assembled view.

FIG. 12A is an exploded view, and FIG. 12B an assembled cross-sectional view.

FIG. 13A is an exploded view, and FIG. 13B an assembled cross-sectional view.

DETAILED DESCRIPTION OF EMBODIMENTS

Figure 1A:
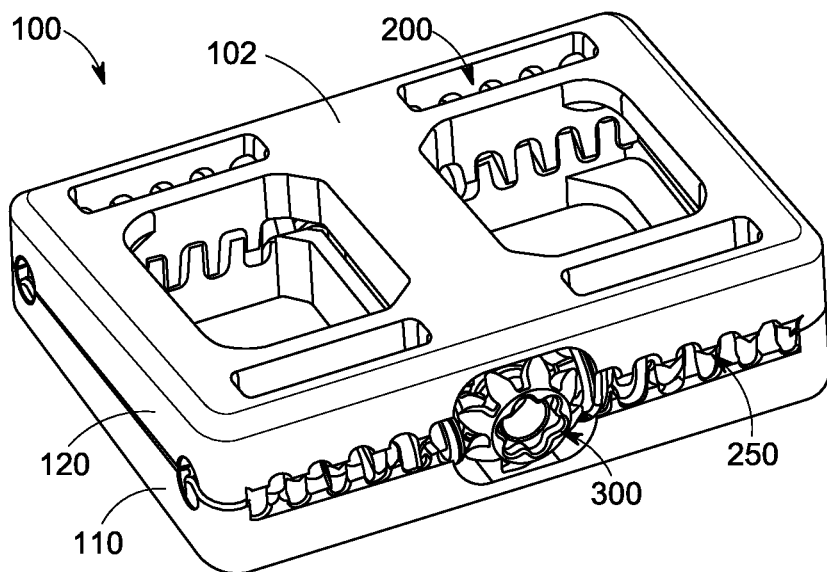
FIGS. 1A-1D depict an example interbody fusion device according to embodiments of the disclosure.
Figure 1B:
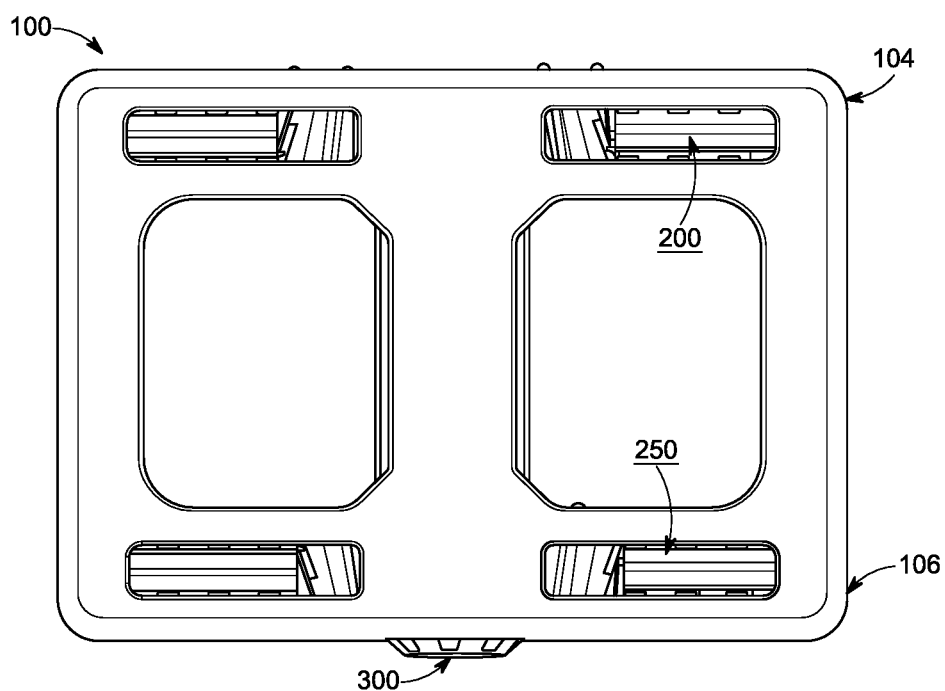

With reference to the figures, where like reference numerals denote like parts, various embodiments of an interbody fusion device will now be described. It should be noted that the figures are only intended to facilitate the description of embodiments and not as an exhaustive description or a limitation on the scope of the disclosure. Further, certain specific details are shown in the figures in order to provide a thorough understanding of various embodiments of the disclosure. One skilled in the art will understand that the claimed invention can be practiced without these details. In other instances, well-known components, structures, or steps associated with the devices and methods of the disclosure may not be shown or described in detail to avoid unnecessarily obscuring the description of embodiments of the disclosure. It should also be noted that certain aspects or features described in conjunction with a particular embodiment are not necessarily limited to that embodiment and can be practiced in any other embodiments.

In general, various embodiments of an interbody fusion device comprise a driving mechanism operable to expand and/or contract the interbody fusion device and a torque transfer mechanism operable to transfer torque to the driving mechanism in a direction non-parallel e.g. perpendicular to the driving mechanism. The interbody fusion device may be a dual-axis adjustable interbody fusion device comprising a first driving mechanism and a second driving mechanism. The first driving mechanism and the second driving mechanism can be operated simultaneously or independently by the torque transfer mechanism, allowing for simultaneous or independent control of the expansion and/or lordotic adjustment of the interbody fusion device. By way of example, an example interbody fusion device in a contracted configuration can be anteriorly inserted in the patient and placed between adjacent vertebrae, with the first driving mechanism of the interbody fusion device being positioned along the posterior side of the patient and and the second driving mechanism of the interbody fusion device being positioned along the anterior side of the patient. The interbody fusion device can be then operated by applying torque anteriorly e.g. to a first transfer mechanism, which is in a direction generally perpendicular to the first driving mechanism that accepts the torque from the first transfer mechanism, in turn allowing the first driving mechanism to convert the torque to a linear motion creating expansion of the interbody fusion on the posterior side, and a second transfer mechanism, which is in a direction generally perpendicular to the second driving mechanism that accepts the torque from the second transfer mechanism, in turn allowing the second driving mechanism to convert the torque to a linear motion creating expansion of the interbody fusion device on the anterior side. These transfer and drive mechanisms allow the intervertebral space at the posterior side and/or anterior side of the patient to be expanded and/or lordotically adjusted, simultaneously or independently, to achieve a desired sagittal balance or correct sagittal imbalance for the patient. While kyphosis (negative lordosis) is not desirable in the lumbosacral segment of the spine, the interbody fusion device of the disclosure can be kyphotically adjusted (negative lordosis) if desired.

With reference to FIGS. 1A-1D, an example interbody fusion device 100 may comprise an expandable housing 102, a first driving mechanism 200, a second driving mechanism 250, and a torque transfer mechanism 300. The first driving mechanism 200 is arranged in the housing 102 at a first lateral area 104 operable to expand and/or contract the housing at the first lateral area 104. The second drive mechanism 250 is arranged in the housing 102 at a second lateral area 106 operable to expand and/or contract the housing at the second lateral area 106. The torque transfer mechanism 300 is operable to receive torque in a direction non-parallel, e.g. generally perpendicular to the first driving mechanism 200 and the second driving mechanism 250 and transfer torque to the first driving mechanism 200 and the second driving mechanism 250. As will be described in greater detail below, the torque transfer mechanism 300 can transmit or translate torque to the first driving mechanism 200 and the second driving mechanism 250 simultaneously or independently, allowing expansion and/or contraction of the housing 102 at the first lateral area 104 and the second lateral area 106 to be controlled simultaneously or independently.

With reference to FIGS. 1A-1D, the housing 102 may include a first or inferior shell member 110 and a second or superior shell member 120. The inferior shell member 110 and the superior shell member 120 may include one or more openings or windows for accepting bone graft material or allowing bone to pass as fusion occurs. The sides or edges of the inferior member 110 and the superior shell member 120 may include chamfered or rounded portions to facilitate insertion of the interbody fusion device 100 into the patient's anatomy. The surfaces of the inferior shell member 110 and the superior shell member 120 may include various features such as serrations, teeth, recesses, dents, etc. to help prevent migration of the device or provide better hold. The surfaces of the inferior shell member 110 and the superior shell member 120 may also include countersink hole features to accept various types of anchors to also help prevent migration and/or further stabilization of the device.

Figure 1C:
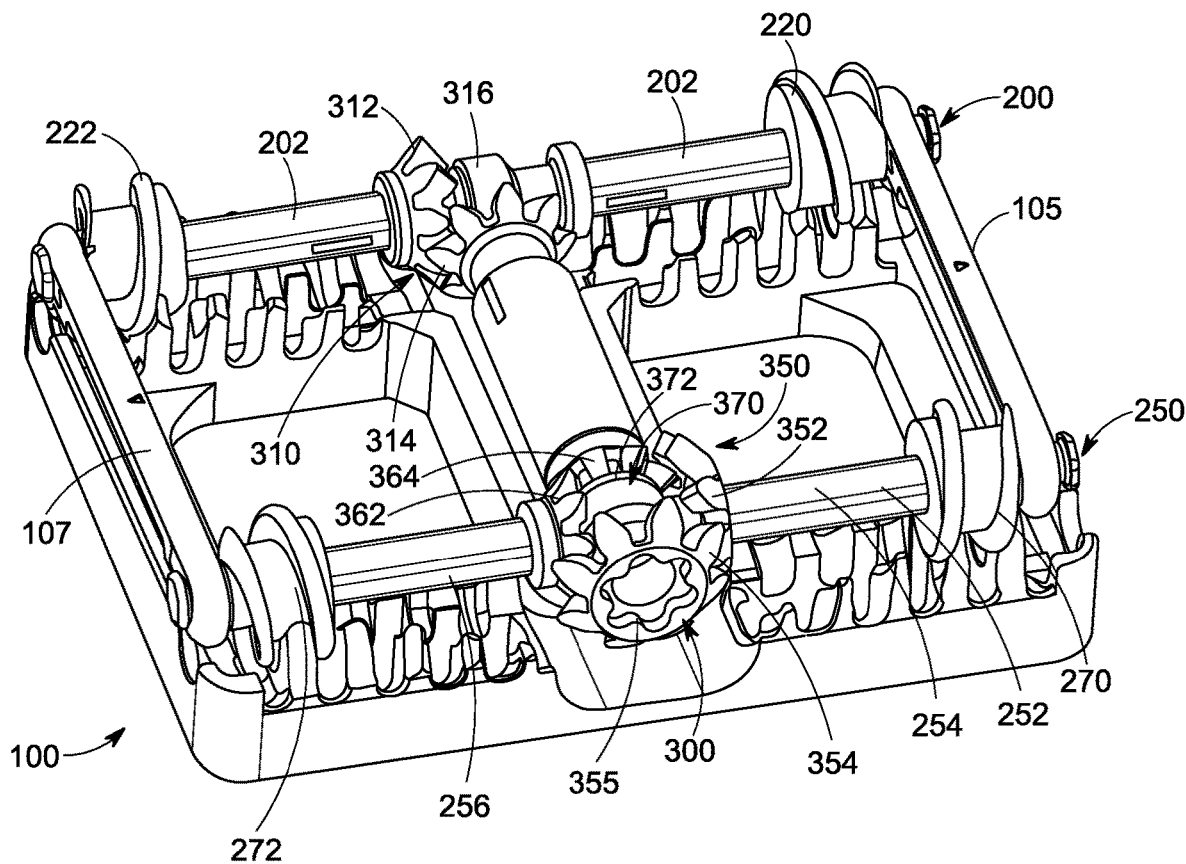
Figure 1D:
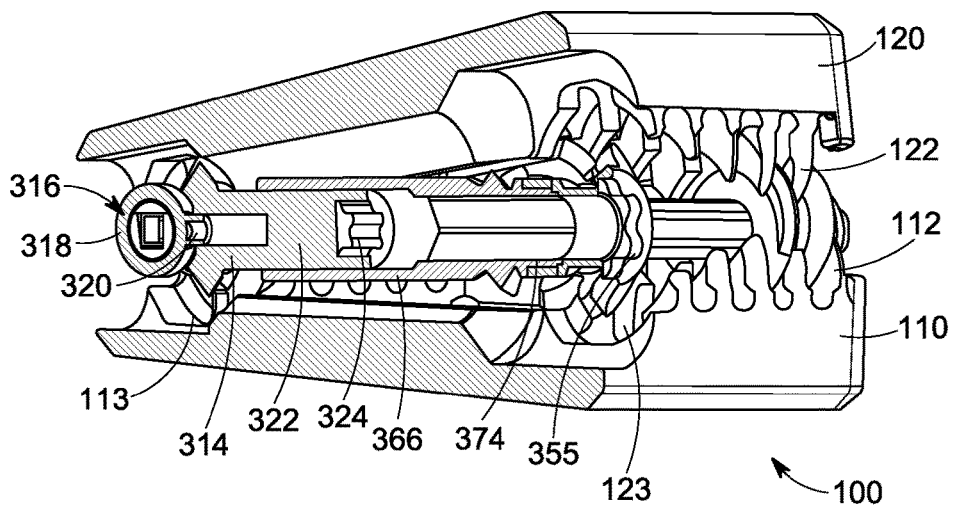

The inferior shell member 110 may include a plurality of individual riser members 112 (FIG. 1D). The superior shell member 120 may include a plurality of individual riser members 122 (FIG. 1D). The plurality of individual riser members 112 of the inferior shell member 110 and the plurality of individual riser members 122 of the superior shell members 120 may define a first step tracking run 113 along a first lateral area 104 of the housing 102 and a second step tracking run 123 along a second lateral area 106 of the housing 102 (FIG. 1D). The height of the plurality of individual riser members 112, 122 may change along the first step tracking run 113 and the second step tracking run 123. For example, the height of the plurality of individual riser members 112, 122 of the first and second step tracking runs 113, 123 may increase successively from a central portion of the step tracking extending distally from the central portion.

With reference to FIGS. 1A-1D, the first driving mechanism 200 may include a first shaft or axle 202 having a longitudinal axis and a first pair of screw members 220, 222. The second driving mechanism 250 may include a second shaft or axle 252 having a longitudinal axis and a second pair of screw members 270, 272. The first axle 202 may be arranged at a first lateral area 104 of the housing 102. The second axle 252 may be arranged at the second lateral side 106 of the housing 102. The first axle 202 and the second axle 252 may be substantially parallel.

The first pair of screw members 220, 222 may each be provided with a through-opening configured to allow the first axle 202 to pass and engage with the first pair of screw members 220, 222. The second pair of screw members 270, 272 may each be provided with a through-opening configured to allow the second axle 252 to pass and engage with the second pair of screw members 220, 222. The second axle 252 may comprise two separate sections 254 and 256 that are assembled, to be described further below. The rotation of the first axle 202 causes the first pair of screw members 220, 222 to rotate and travel on the first step tracking run 113 defined by the individual riser members 112, 122 on the inferior and superior shell members 110, 120, converting the rotational motion into linear motion. The rotation of the second axle 252 causes the second pair of screw members 270, 272 to rotate and travel on the second step tracking run 123 defined by the individual riser members 112, 122 on the inferior and superior shell members 110, 120, converting the rotational motion into linear motion. In response to the linear movement of the first pair of screw members 220, 222 as they advance along and on the individual on the individual risers 112, 122, the inferior shell member 110 and the superior shell member 120 move linearly relative to each other, effecting expansion or contraction of the housing 102 at the first lateral area 104. Likewise, in response to the linear movement of the second pairs of screw members 270, 272 as they advance along and on the individual risers 112, 122, the inferior shell member 110 and the superior shell member 120 move linearly relative to each other, effecting expansion or contraction of the housing 102 at the second lateral area 106. As will be described in greater detail below, the first axle 202 and the second axle 252 can be operated or rotated by the torque transfer mechanism 300 simultaneously and independently. Therefore, a degree of expansion or contraction of the housing 102 at the first lateral area 104 can be simultaneously or independently adjusted relative to a degree of expansion or contraction of the housing 102 at the second lateral area 106 when the first pair of screw members 220, 222 and the second pair of screw members 270, 272 are rotated to different positions on the first tracking run 113 and second step tracking run 123.

The first pair of screw members 220, 222 may be configured and/or arranged such that the directional orientation of the helical thread of the screw member 220 is opposite to the directional orientation of the screw member 222 so that the screw members 220, 222 of the first pair move in an opposite direction relative to each other upon rotation of the first axle 202. Similarly, the second pair of screw members 270, 272 may be configured and/or arranged such that the directional orientation of the helical thread of the screw member 270 is opposite to the directional orientation of the helical thread of the screw member 272 so that the screw members of the second pair move in an opposite direction relative to each other upon rotation of the second axle 252.

The first pair of screw members 220, 222 and the second pair of screw members 270, 272 may each have a tapered configuration and comprise a root surface and a helical thread. The root surface of a screw member may provide a contact surface for a riser member. The helical thread of a screw member can be configured to be received in the gap between adjacent riser members. The first pair of screw members 220, 222 and the second pair of screw members 270, 272 may each have a variable root radius and/or a helical thread with a variable thickness that are similar or different in size with respect to one another. A variable root radius and thread thickness can create a tighter fit between the screw members and the individual riser members, which in turn reduces, minimizes, or eliminates unwanted micromotion between parts when the interbody fusion device is in its starting position, expanded position or lordotically adjusted position. Various embodiments of screw members are described in U.S. Pat. Nos. 9,889,019, 10,188,527, and U.S. application Ser. No. 16/569,621 filed Sep. 12, 2019 entitled "Expandable and Adjustable Lordosis Interbody Fusion System." The disclosures of U.S. Pat. Nos. 9,889,019 and 10,188,527, and U.S. Ser. No. 16/569,621 are incorporated herein by reference in their entirety.

The positions of the plurality of individual riser members 112 on the inferior shell member 110 may be arranged to offset from the positions of the plurality of individual riser members 122 on the superior shell member 120 so that the plurality of individual riser members 112 of the inferior shell member 110 may intermesh the plurality of individual riser members 122 of the superior shell member 120 when the interbody fusion device 100 is in a contraction configuration.

With reference to FIGS. 1A-1D, the torque transfer mechanism 300 allows for application of torque to the first driving mechanism 200 and the second driving mechanism 250 in a direction non-parallel e.g. generally perpendicular to the longitudinal axis of the first axle 202 of the first driving mechanism 200 or the longitudinal axis of the second axle 252 of the second driving mechanism 250. As better viewed in FIG. 1C, the torque transfer mechanism 300 may include a first gear assembly 310 operable to receive and transfer torque to the first driving mechanism 200, and a second gear assembly 350 operable to receive and transfer torque to the second driving mechanism 250.

The first gear assembly 310 may include a translating gear 312 and a driving gear 314. The translating gear 312 may be coupled or fixedly coupled to the first axle 202 of the first driving mechanism 200. The first axle 202 may be a single component or comprise two separate sections that are press-fit and/or welded together to form a single component. The translating gear 312 may be configured to receive torque from the driving gear 314 and rotate, causing the first axle 202 to rotate. The rotation of the first axle 202 causes the first pair of screw members 220, 222 to rotate and move on the individual riser members, causing the first and second shell members 110, 120 to move linearly relative to each other thereby expanding and/or contracting the housing 102 at the first lateral area 104. The driving gear 314 may be configured to receive torque applied in a direction non-parallel e.g. generally perpendicular to the first axle 202, and transfer torque to the translating gear 312. As shown, the driving gear 314 may be coupled to the first axle 202 via a connection member 316 (FIGS. 1C and 1D). For example, the connection member 316 may comprise a ring 318 received on a rounded portion of the first axle 202, and an arm 320 extended from the ring 318 and received in the driving gear 314. The arm 320 may be threaded or unthreaded to allow the driving gear 314 to rotate about the axes of the arm 320 of the connection member 316 and restrict off axis motion while transferring torque to the translating gear 312. The driving gear 314 may have an elongate portion 322 configured to be rotatably received in a sleeve section of a driving gear in the second gear assembly 350 (FIG. 1D), to be described in greater detail below. The end of elongate portion 322 of the driving gear 314 of the first gear assembly 310 may be provided with a feature e.g. a female hexalobe 324 for engaging with a driver in a surgical instrument to be described in greater detail below.

The translating gear 312 and the driving gear 314 of the first gear assembly 310 may be various types of bevel gears such as straight, spiral, zerol bevel, hypoid, or spiroid. By way of example, the translating gear 312 and the driving gear 314 may have a pitch e.g. 8 mm. Other gear sizes are apparently possible, and the present claims are not so limited. In certain embodiments, the principle of the disclosure can be implemented with worm gears.

The second gear assembly 350 may include a first translating gear 352 and a first driving gear 354. The second gear assembly 350 may further include a second translating gear 362 and a second driving gear 364. In certain embodiments of the disclosure, the second axle 252 may include a first section 254 operating with a screw member 270 and a second section 256 operating with a screw member 272. Therefore, the first translating gear 352 of the second gear assembly 350 may be coupled to the first section 254 of the second axle 252 and configured to rotate the first section 254. Rotation of the first section 254 of the second axle 252 causes the screw member 270 to rotate and travel on the individual riser members. The second translating gear 262 of the second gear assembly 350 may be coupled to the second section 256 of the second axle 252 and configured to rotate the second section 256. Rotation of the second section 256 of the second axle 252 causes the screw member 272 to rotate and travel along and on the individual riser members. The first section 254 and the second section 256 of the second axle 252 may be rotatably connected to a connection member 370. For example, the connection member 370 may comprise a ring 372, a first arm (not shown) extended from the ring and received in the first section 254 of the second axle 252, and a second arm (not shown) extended from the ring and received in the second section 256 of the second axle 252. The first arm and the second arm may be threaded or unthreaded to allow the first section 254 and the second section 256 of the second axle 252 to rotate respectively about the axes of the connection member 370 and first arm and second arm while restricting off axis motion.

The first driving gear 354 of the second gear assembly 350 may be configured to receive torque applied in a direction non-parallel e.g. generally perpendicular to the second axle 352, and transfer torque to the first translating gear 352 of the second gear assembly 350. The second driving gear 364 of the second gear assembly 350 may be configured to receive torque applied in a direction non-parallel e.g. generally perpendicular to the second axle 252, and transfer torque to the second translating gear 362 of the second gear assembly 350. For example, the first driving gear 354 may include a feature e.g. a female hexalobe 355 configured to engage with a driver in a surgical instrument for receiving torque in a direction generally perpendicular to the second axle 252. In certain embodiments, the first driving gear 354 and the second driving gear 364 of the second gear assembly 350 may be constructed or assembled to operate as a single unit such that a rotation of the first driving gear 354 allows a rotation of the second driving gear 364. For example, the first driving gear 354 and the second driving gear 364 may be connected to form a tubular section 374, which may be received in the ring 372 of the connection member 370, allowing the first driving gear 354 and the second driving gear 364 to rotate as a single unit (FIG. 1D). Alternatively, the first driving gear 354 and the second driving gear 364 may be disconnected to form a section with a gap where the section 374 is present to allow for independent adjustment in turn allowing for independent or unequal rotations of axle section 254 and 256, allowing the screw members 270 and 272 to rotate and travel along and on the individual riser members at different locations with respect to one another.

The first driving gear 354 and the first translating gear 352 of the second gear assembly 350 may be various classifications and types of bevel gears. The second driving gear 364 and the second translating gear 362 of the second gear assembly 350 may be various classifications and types of bevel gears. The first driving gear 354 and the second driving gear 364 may have a different pitch. For example, the first driving gear 354 may have a pitch e.g. 8 mm and the second driving gear 364 may have a pitch e.g. 6 mm. As such, the first translating gear 352 may have a pitch e.g. 8 mm and the second translating gear 362 may have a pitch e.g. 6 mm. Other gear sizes are apparently possible and the present claims are not so limited. Alternatively, the first driving gear 354 and the second driving gear 364 may have a same pitch, and the first translating gear 352 and the second translating gear 362 may have a same pitch. In certain embodiments, the principle of the disclosure can be implemented with worm gears.

In certain embodiments, the torque transfer mechanism 300 can be configured to allow a surgical instrument to operate the first gear assembly 310 and the second gear assembly 350, either simultaneously or independently. As better viewed in FIGS. 1C and 1D, the driving gear 314 of the first gear assembly 310 may include an elongate portion 322. The second driving gear 364 of the second gear assembly 350 may include a sleeve section 366. The elongate portion 322 of the driving gear 314 of the first gear assembly 310 can be rotatably received in the sleeve section 366 of the second driving gear 364 of the second gear assembly 350. This allows a surgical instrument having two drivers, e.g. a male hexalobe driver within a female hexalobe driver, to operate the first gear assembly 310 and the second gear assembly 350 simultaneously and independently. As such, the first driving mechanism 200 and the second driving mechanism 250 of the interbody fusion device 100 can be operated either simultaneously or independently by the surgical instrument via the first gear assembly 310 and the second gear assembly 350 respectively. By way of example, the end of the elongate portion 322 of the driving gear 314 of the first gear assembly 310 may be provided with a feature 324 e.g. a female hexalobe for engaging with a first driver having e.g. a male hexalobe feature. The channels in the first driving gear 354 and the second driving gear 364 including the sleeve section 366 allow the first driver in the surgical instrument to access to the female hexalobe feature 324 in the driving gear 314 of the first gear assembly 310. The first driving gear 354 of the second gear assembly 350 may be provided with a feature 355 e.g. a female hexalobe feature configured for engaging with a second driver having e.g. an external hexalobe feature.

Figure 2A:
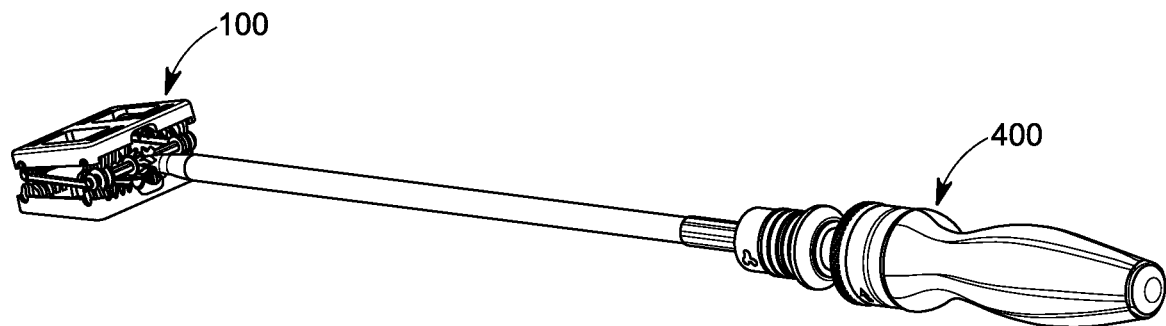
FIGS. 2A-2C depict an example interbody fusion device of the disclosure in conjunction with a surgical instrument.
Figure 2B:
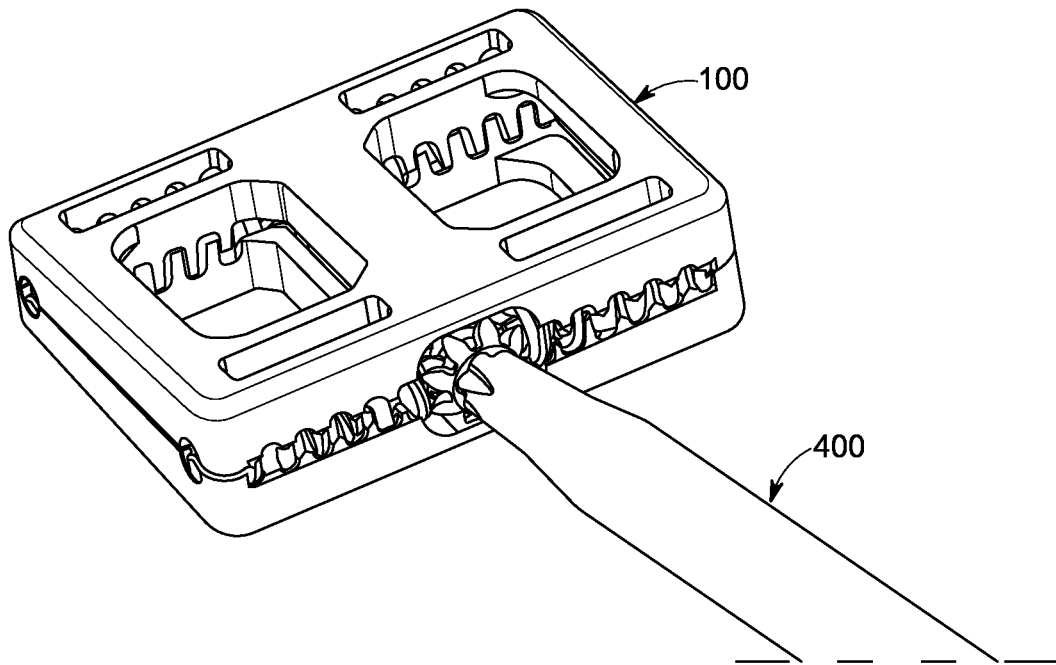
Figure 2C:
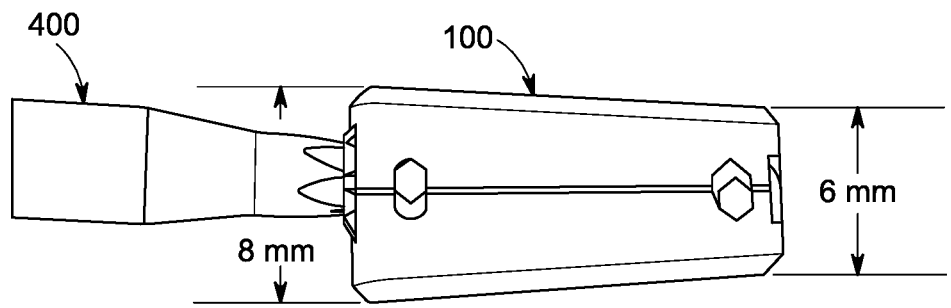

FIGS. 2A-2C show a surgical instrument 400 which can used in operating an example interbody fusion device 100 of the disclosure. FIGS. 3A-3D illustrate engagement of a surgical instrument 400 with an example dual-axis interbody fusion device 100 of the disclosure. Various operating modes can be achieved through different optional adjustment combinations of the two axes of the interbody fusion device that correlate with two directions of the body perpendicular to the two desired directions of the body expansion and/or contraction of the interbody fusion device is desired. For example, adjusting the posterior and anterior axes simultaneously or independently to create expansion in the superior and inferior directions equally or unequally of the interbody fusion device respectively. As better viewed in FIG. 3A-3D, the surgical instrument 400 may include a first driver 410 and a second driver 420. The first driver 410 may be rotatably received in a channel in the second driver 420, and can be extended out and retracted into the channel in the second driver 420, allowing the first driver 410 to apply torque independently of or simultaneously with the second driver 420. The first driver 410 of the surgical instrument 400 may include a working end portion having a feature e.g. a male hexalobe for engaging with the driving gear 314 of the first gear assembly 310 which may include an end having a feature e.g. the female hexalobe. The second driver 420 of the surgical instrument 400 may include a working end portion having a feature e.g. an external hexalobe feature for engaging the first driving gear 354 of the second gear assembly 350 which may have a feature e.g. a female hexalobe.

Figure 3A:
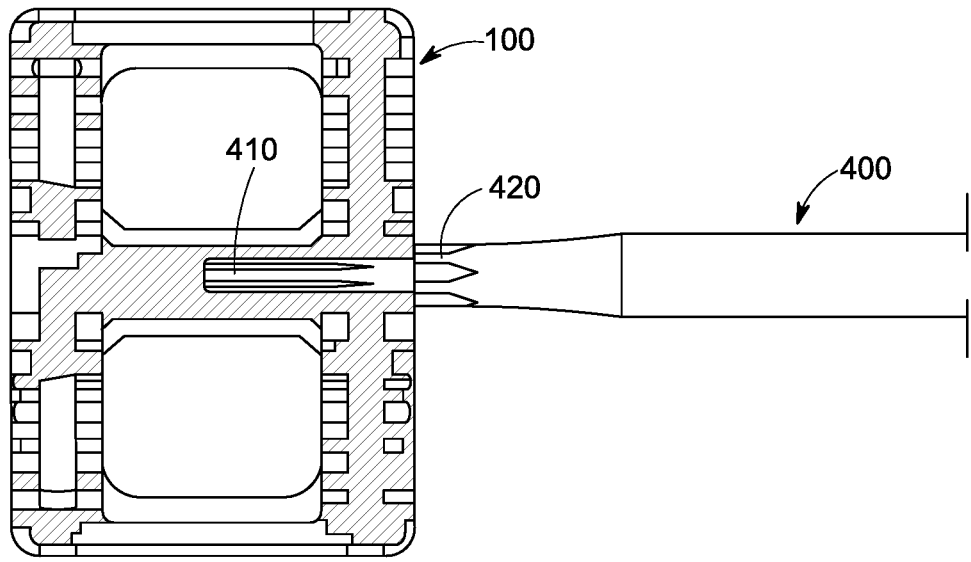
FIGS. 3A-3D illustrate engagement of an example dual-axis interbody fusion device of the disclosure with a surgical instrument in various operating modes.
Figure 3B:
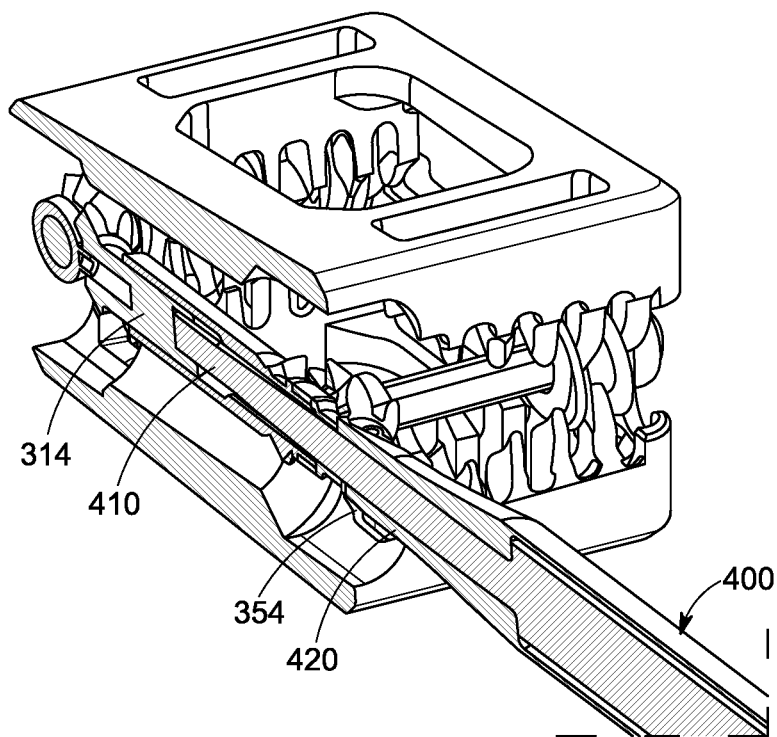

With reference to FIG. 3B, the first driver 410 of the surgical instrument 400 can be extended to allow the first driver 410 to engage the driving gear 314 of the first gear assembly 310, and the second driver 420 to engage the first driving gear 354 of the second gear assembly 350. Operating or turning the first driver 410 and the second driver 420 of the surgical instrument 400 simultaneously allows application of torque to the first gear assembly 310 and the second gear assembly 350 simultaneously, which in turn transfer torque to or actuate the first driving mechanism 200 and the second driving mechanism 250 of the interbody fusion device 100 simultaneously, effecting expansion or contraction of the interbody fusion device 100 at both the posterior side 104 and the anterior side 106. With reference FIG. 3C, the first driver 410 of the surgical instrument 400 may be retracted to disengage the driving gear 314 of the first gear assembly 310, allowing only the second driver 420 of the surgical instrument 400 to engage the first driving gear 354 of the second gear assembly 350. Operating or turning the second driver 420 of the surgical instrument 400 allows application of torque to the second gear assembly 350 only, which in turn transfer torque to or actuate the second driving mechanism 250 of the interbody fusion device 100 only, thereby effecting expansion or contraction of the interbody fusion device 100 at the anterior side 106. With reference to FIG. 3D, the first driver 410 of the surgical instrument 400 may be extended to engage the driving gear 314 of the first gear assembly 310, and the second driver 420 of the surgical instrument 400 may be retracted to disengage the first driving gear 354 of the second gear assembly 350. Operating or turning the first driver 410 of the surgical instrument 400 allows application of torque to the first gear assembly 310 only, which in turn transfer torque to or actuate the first driving mechanism 200 of the interbody fusion device 100 only, thereby effecting expansion or contraction of the interbody fusion device 100 at the posterior side 104.

Returning to FIG. 1C, the interbody fusion device 100 may include a first thrust bearing 105 coupling the first axle 202 and the second axle 252 at a first end of the first axle 202 and a first end of the second axle 252. Additionally, or alternatively, the interbody fusion device 100 may include a second thrust bearing 107 coupling the first axle 202 and the second axle 252 at a second end of the first axle 202 and a second end of the second axle 202. The first thrust bearing 105 and/or the second thrust bearing 107 may be constructed to include two pieces, which can join together by e.g. press fit and/or welding. The first thrust bearing 105 and/or the second thrust bearing 107 allow the first axle 202 rotate about the longitudinal axis of the first axle and prohibit translational or linear movement of the first axle. Likewise, the first thrust bearing 105 and/or the second thrust bearing 107 allow the first section 254 and the second section 255 of the second axle 252 to rotate about the longitudinal axis of the second axle and prohibit translational or linear movement of the first section 254 and the second section 256 of the second axle 252.

The interbody fusion device 100 or at least a part of the interbody fusion device 100 may be constructed from a material comprising metal such as titanium, tantalum, stainless steel, cobalt chrome, or any other biocompatible metal, or alloy. The interbody fusion device 100 or a part of the interbody fusion device 100 may also be constructed from a polymeric material such as poly-ether-ether-ketone (PEEK), poly-ether-ketone-ketone (PEKK), poly-ether-ketone (PEK), and so on.

The interbody fusion device 100 can be in any size suitable for spinal fusion procedures. By way of example, the distance from an end to another end of the device 100 along the first or second driving mechanism 200, 250 ("length") may range from 25 to 60 millimeters (mm). The distance from one lateral side of the device to the opposite lateral side ("width") may range from 20 mm to 35 mm. The device may be manufactured in numerous offerings with different lengths and widths in various increments, for example, 2 mm increments in width and 5 mm increments in length. The distance from the inferior shell member surface to the superior shell member surface of the interbody fusion device in a fully contracted configuration ("base height") may range from 5 mm to 10 mm. The interbody fusion device may have different base heights or starting heights at the anterior side and the posterior side. For example, the base height at the posterior side may be smaller than the base height at the anterior side to accommodate to the nature of the anterior surgery to allow for a deeper device to fit into the intervertebral space, as shown in FIG. 2C. A contracted configuration with different starting heights at the posterior side and the anterior side may also help prevent against device subsidence and better meet the anatomy of the human spine. Alternatively, the interbody fusion device 100 may have a same or similar base height at both the anterior side and the posterior side. The dual-axis driving mechanisms according to embodiments of the disclosure can provide a continuous expansion in height ranging from 0 mm to 9 mm and a continuous angulation between the inferior and superior shell member surfaces ("lordosis") ranging from 0-30 degrees. It should be noted that the above specific dimensions are provided for thorough understanding of various aspects of the disclosure but are not intended to limit the scope of the claims. Other dimensions are apparently possible to one of ordinary skill.

Example 1: Expansion Mode (Simultaneous Dual-Axis Adjustments)

Figure 4:
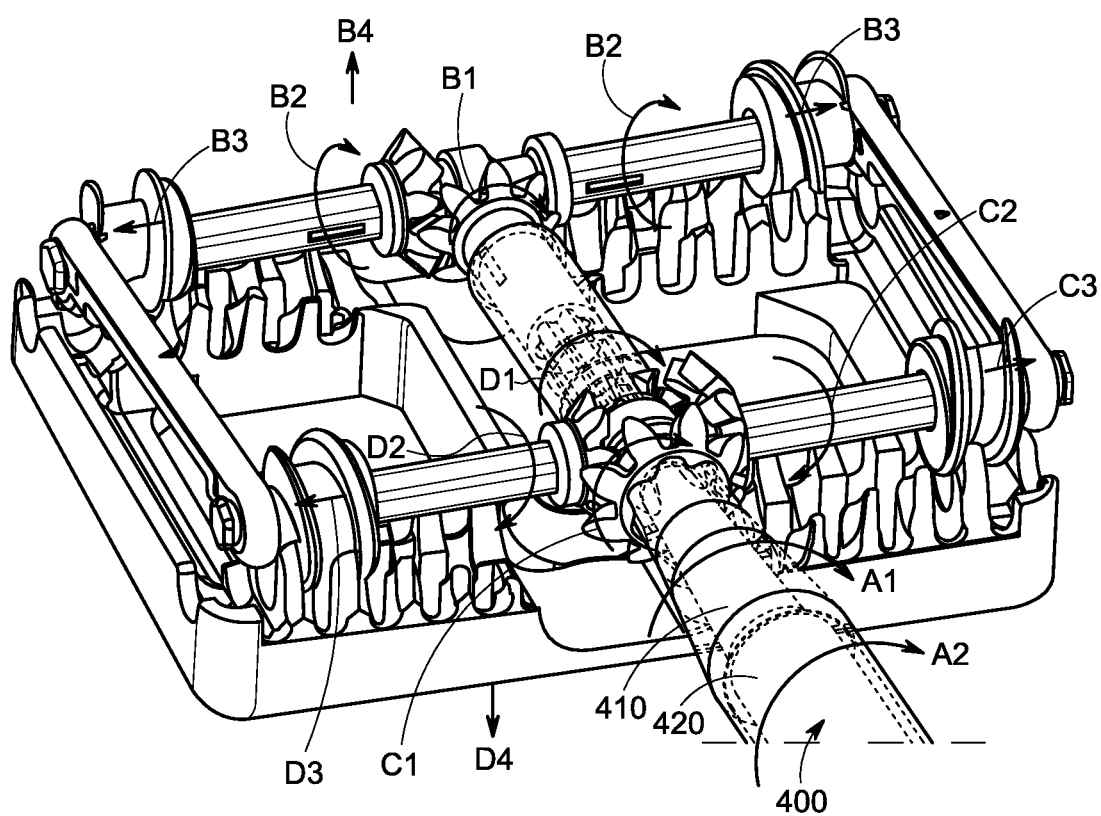
FIG. 4 is a partially exploded view of an example interbody fusion device illustrating simultaneous adjustment of both sets of driving gears and axles (simultaneous dual-axis adjustment) of the interbody fusion device together in turn driving both translating axles together creating a parallel expansion operating mode.

With reference to FIGS. 4 and 1C, an expansion mode of an example interbody fusion device 100 will now be described. In the expansion mode, the first driving mechanism 200 and the second driving mechanism 250 of the interbody fusion device 100 can be operated simultaneously, providing parallel expansion or contraction of the interbody fusion device 100.

The interbody fusion device 100 in a starting or contracted configuration can be first placed in the intervertebral space via an anterior surgical procedure. To begin with the expansion mode, the user may use a surgical instrument 400 including a first driver 410 and the second driver 420 as shown in FIGS. 2A-2C and 3A-3D, allowing the first driver 410 to engage the driving gear 314 of the first gear assembly 310, and the second driver 420 to engage the first driving gear 354 of the second gear assembly 350, as better shown in FIG. 3B. The user may then apply torque in a direction generally perpendicular to the driving mechanisms 200, 250 of the interbody fusion device 100, by turning both the first driver 410 and the second driver 420 of the surgical instrument 400, e.g. in the clockwise direction, as indicated by arrow A1 and arrow A2 in FIG. 4.

With reference to FIGS. 4 and 1C, the turning of the first driver 410 of the surgical instrument 400 causes the driving gear 314 of the first gear assembly 310 to rotate e.g. in the clockwise direction as indicated by arrow B1, which in turn drives the translating gear 312 e.g. in the outward direction as indicated by arrow B2, causing the first axle 202 to rotate e.g. in the outward direction as indicated by arrow B2. The rotation of the first axle 202 causes the screw members 220, 222 to travel on the riser members e.g. in the outward directions as indicated by arrow B3, causing the inferior shell member 110 and the superior shell member 120 of the interbody fusion device 100 to move linearly relative to each other, e.g. expand, at the posterior side 104 as indicated by arrow B4.

With reference to FIGS. 4 and 1C, the turning of the second driver 420 of the surgical instrument 400 causes the first driving gear 354 of the second gear assembly 350 to rotate e.g. in the clockwise direction, as indicated by arrow C1, which in turn drives the first translating gear 352 e.g. in the outward direction as indicated by arrow C2, causing the first section 254 of the second axle 252 to rotate e.g. in the outward direction as indicated by arrow C2. The rotation of the first section 254 of the second axle 252 causes the screw member 270 to travel on the riser members e.g. in the outward direction as indicated by arrow C3.

Still with reference to FIGS. 4 and 1C, the turning of the second driver 420 of the surgical instrument 400 also causes the second driving gear 364 of the second gear assembly 350 to rotate e.g. in the clockwise direction, as indicated by arrow D1, which in turn drives the second translating gear 362 e.g. in the outward direction as indicated by arrow D2, causing the second section 256 of the second axle 252 to rotate e.g. in the outward direction as indicated by arrow D2. The rotation of the second section 256 of the second axle 252 causes the screw member 272 to travel on the riser members e.g. in the outward direction as indicated by arrow D3.

The movement of the screw member 270 on the first section 254 of the second axle 252 and the screw member 272 on the second section 256 of the second axle 252 causes the inferior shell member 110 and superior shell member 120 to move linearly relative to each other, e.g. expand, at the anterior side as indicated by arrow D4.

Figure 7:
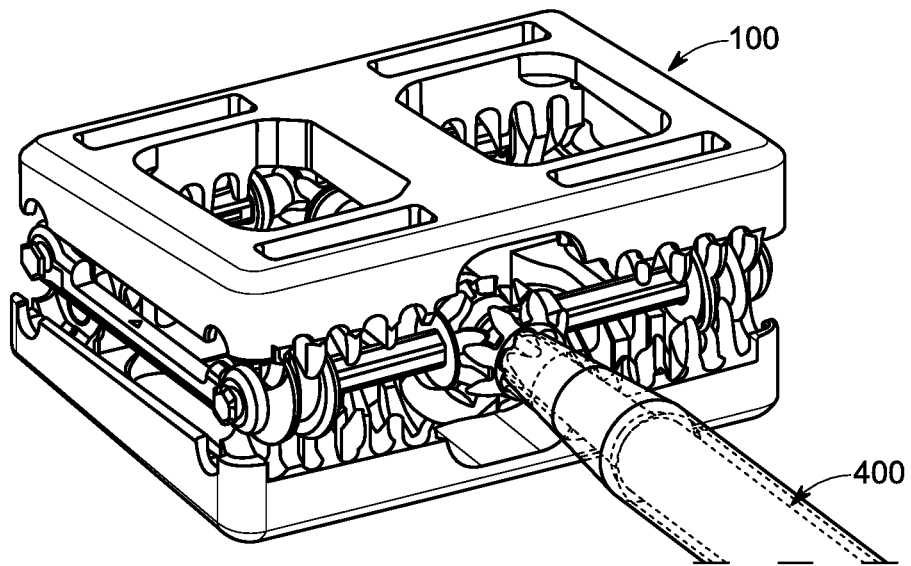
FIG. 7 depicts an example interbody fusion device in an expanded configuration.

It should be noted that while the operations of the driving gear 314 and translation gear 312 of the first gear assembly 310, the first driving gear 354 and second driving gear 364 of the second gear assembly 350, the first translating gear 352 and the second translating gear 362 of the second gear assembly 350, and first driving mechanism 200 and second driving mechanism 250 are described in sequential steps for clarity, the rotation, translation, or movement of the above assemblies, mechanisms or parts of the mechanisms occur simultaneously upon turning the first driver 410 and the second driver 420 of the surgical instrument 400 simultaneously. The example illustrated in FIG. 4 expands the interbody fusion device 100 at both the posterior side 104 and the anterior side 106 by turning the first driver 410 and the second driver 420 of the surgical instrument 400 simultaneously e.g. in the clockwise direction. A reverse operation by turning the first driver 410 and the second driver 420 in the counterclockwise direction may contract the interbody fusion device 100 from the expanded configuration. FIG. 7 is an isometric view showing an expanded configuration of the interbody fusion device 100.

Example 2: Lordosis Mode (Independent Anterior Axis Adjustment)

Figure 5:
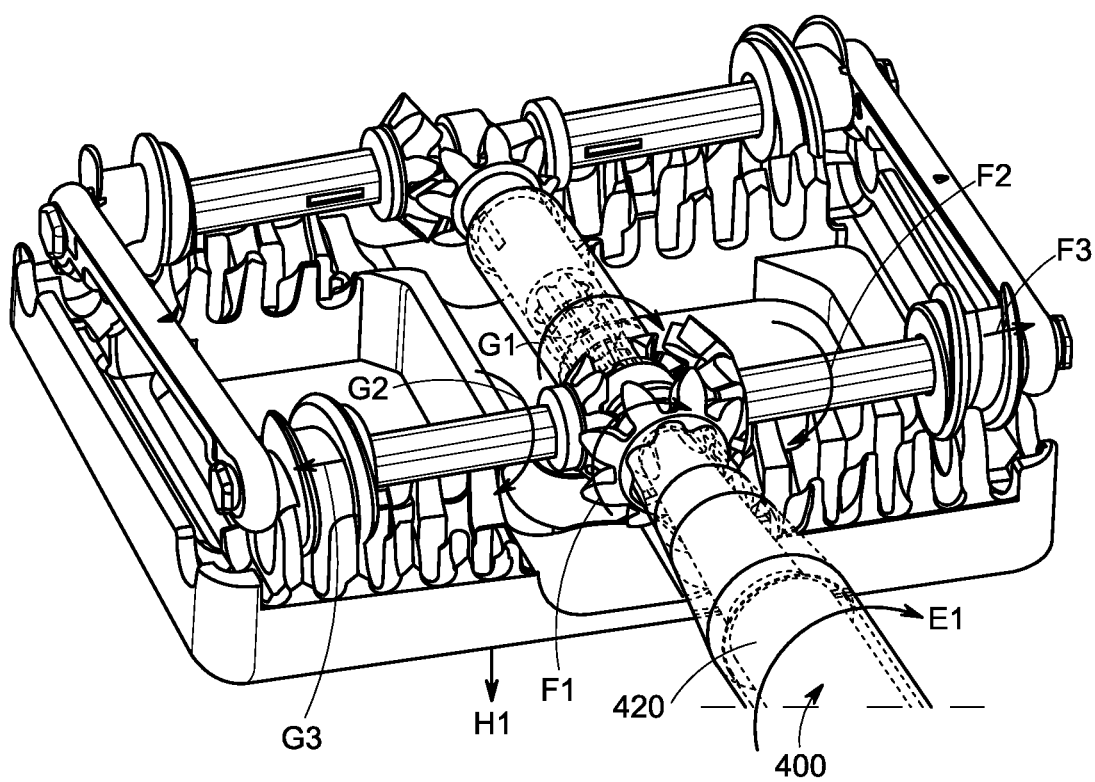
FIG. 5 is a partially exploded view of an example interbody fusion device illustrating independent operation of only the driving gears and axles within the second lateral portion (independent anterior axis adjustment) of the interbody fusion device in turn driving only the translating axle in the second lateral portion of the interbody device creating unequal expansion or a lordosis operating mode.

With reference to FIGS. 5 and 1C, a lordosis mode, or independent adjustment of the anterior axis of an example interbody fusion device 100 will now be described. In this lordosis mode, the second driving mechanism 250 of an interbody fusion device 100 can be operated independently of the first driving mechanism 100, lordotically adjusting the configuration of the interbody fusion device 100 at the anterior side 106. A lordosis mode of the interbody fusion device 100 may be desired to provide an offset in expansion between the anterior side 104 and posterior side 106 of the interbody fusion device 100. The anterior side 104 can be expanded and/or contracted to a point below the posterior side 106 resulting in negative lordosis (kyphosis).

Figure 3C:
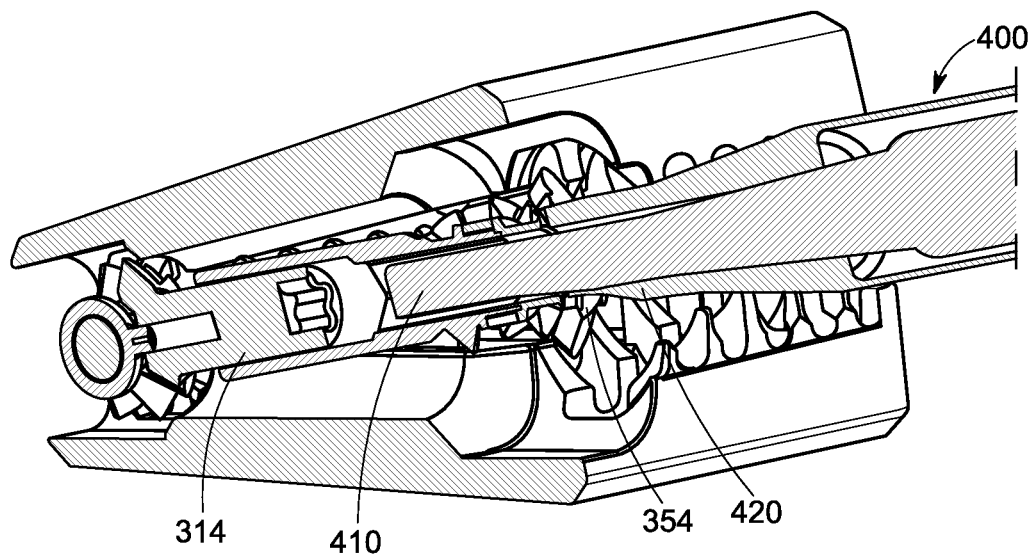
Figure 3D:
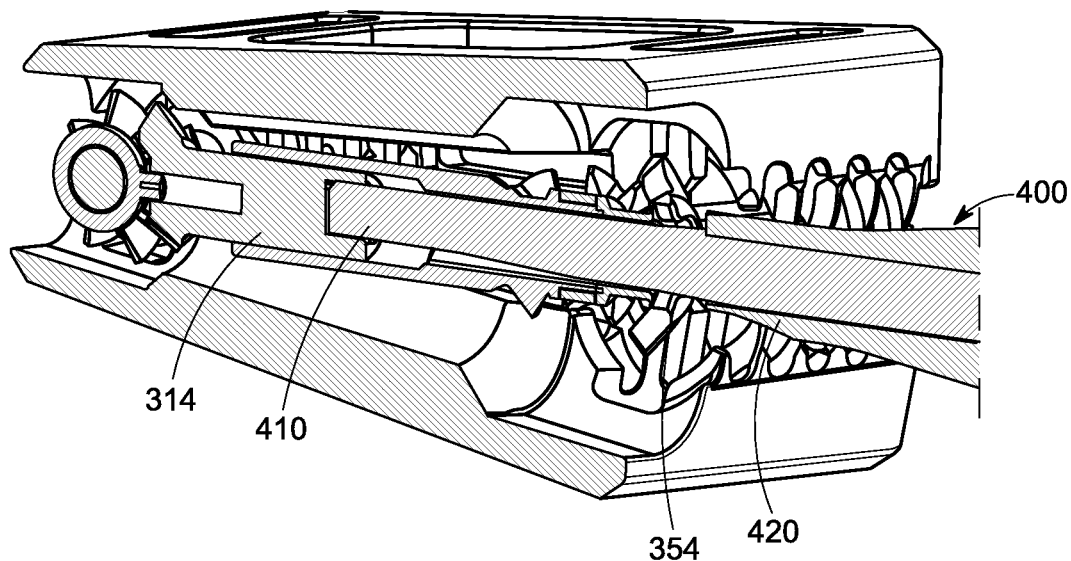

To begin with the lordosis mode, the user may extend only the second driver 420 of the surgical instrument 400, allowing only the second driver 420 to engage with the first driving gear 354 of the second gear assembly 350, as shown in FIG. 3C. If the first driver 410 of the surgical instrument 400 had been inserted across the entire span of the interbody fusion device during the expansion mode, the first driver 410 can be retracted to the point shown in FIG. 3C in order to operate only the anterior side 106 of the interbody fusion device 100 independently. A marking on the surgical instrument 400 can be provided to help indicate how far the first driver 410 can be inserted in the interbody fusion device 100 for the lordosis mode. Then, the user may apply torque in a direction generally perpendicular to the second driving mechanism 250 of the interbody fusion device 100 by turning the second driver 420 e.g. in the clockwise direction, as indicate by arrow E1.

With reference to FIGS. 5 and 1C, the turning the second driver 420 of the surgical instrument 400 causes the first driving gear 354 of the second gear assembly 350 to rotate e.g. in the clockwise direction as indicated by arrow F1, which in turn drives the first translating gear 352 e.g. in the in the outward direction as indicated by arrow F2, causing the first section 254 of the second axle 252 to rotate e.g. in the outward direction as indicated by arrow F2. The rotation of the first section 254 of the second axle 252 causes the screw member 270 to travel on the riser members e.g. in the outward direction as indicated by arrow F3.

The turning the second driver 420 of the surgical instrument 400 also causes the second driving gear 364 of the second gear assembly 350 to rotate e.g. in the clockwise direction as indicated by arrow G1, which in turn drives the second translating gear 362 e.g. in the outward direction as indicated by arrow G2, causing the second section 256 of the second axle 252 to rotate e.g. in the outward direction as indicated by arrow G2. The rotation of the second section 256 of the second axle 252 causes the screw member 272 to travel on the riser members e.g. in the outward direction as indicated by arrow G3. In certain embodiments, the first driving gear 354 and the second driving gear 364 can be modified in which a gap between both components exists when assembled, with the first driving gear 354 having an increased overall diameter. The first driving gear female hexalobe mating geometry that mates with the second driver 420 of the surgical instrument 400 may be modified to allow the second driver 420 to pass completely through the first driving gear 354 and reach the second driving gear 364. This modified design configuration would allow for unequal expansion adjustments between the screw member 270 and the screw member 272 across the coronal plane, allowing for corrections with patients possessing deformities such as scoliosis.

The movement of the screw members 270, 272 on the individual riser members causes the first shell member 110 and the second shell member 120 to linearly move relative to each other or expand at the anterior side 106, lordotically adjusting the interbody fusion device 100 at the anterior side 106, as indicated by arrow H1. Completing all of the previously described movements of the components in the reverse directions to create a contracted adjustment of the anterior side 106 to a point below the posterior side 104, would kyphotically adjust (negative lordosis) the interbody fusion device 100.

Figure 8:
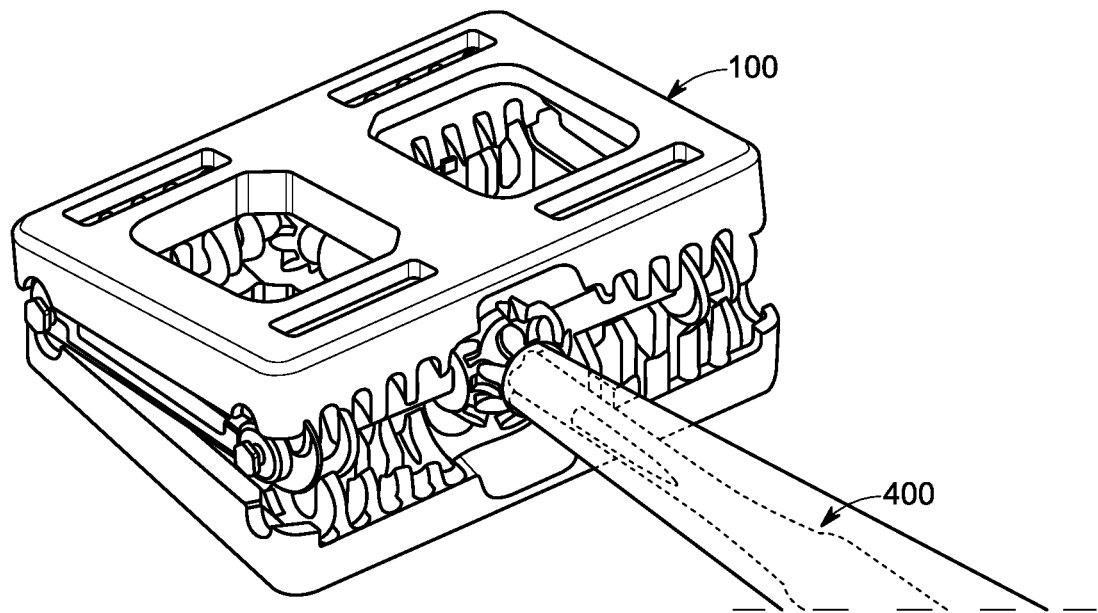
FIG. 8 depicts an example interbody fusion device in a lordotically adjusted configuration.

It should be noted that while the operations of the first driving gear 354 and second driving gear 364 of the second gear assembly 350, and the first translating gear 352 and the second translating gear 362 of the second gear assembly 350, and the second driving mechanism 250 are described in sequential steps for clarity, the above assemblies, mechanisms or parts are operated simultaneously upon turning of the second driver 420 of the surgical instrument 400. Further, the example shown in FIG. 5 lordotically adjusts the interbody fusion body 100 or expands the device at the anterior side 106 by turning the second driver 420 of the surgical instrument 400 in the clockwise direction. The interbody device may also operate adequately if inverted or inserted into the intervertebral disc space upside down. Correct operation of the interbody device in this inverted position can be achieved by reversing the applied torque and through rotating the second driver 420 e.g. in the counterclockwise direction may adjust the degree of the lordosis of the interbody fusion device 100. FIG. 8 is an isometric view showing a lordotically adjusted configuration of the interbody fusion device 100.

Example 3: Lordosis Mode (Independent Posterior Axis Adjustment)

Figure 6:
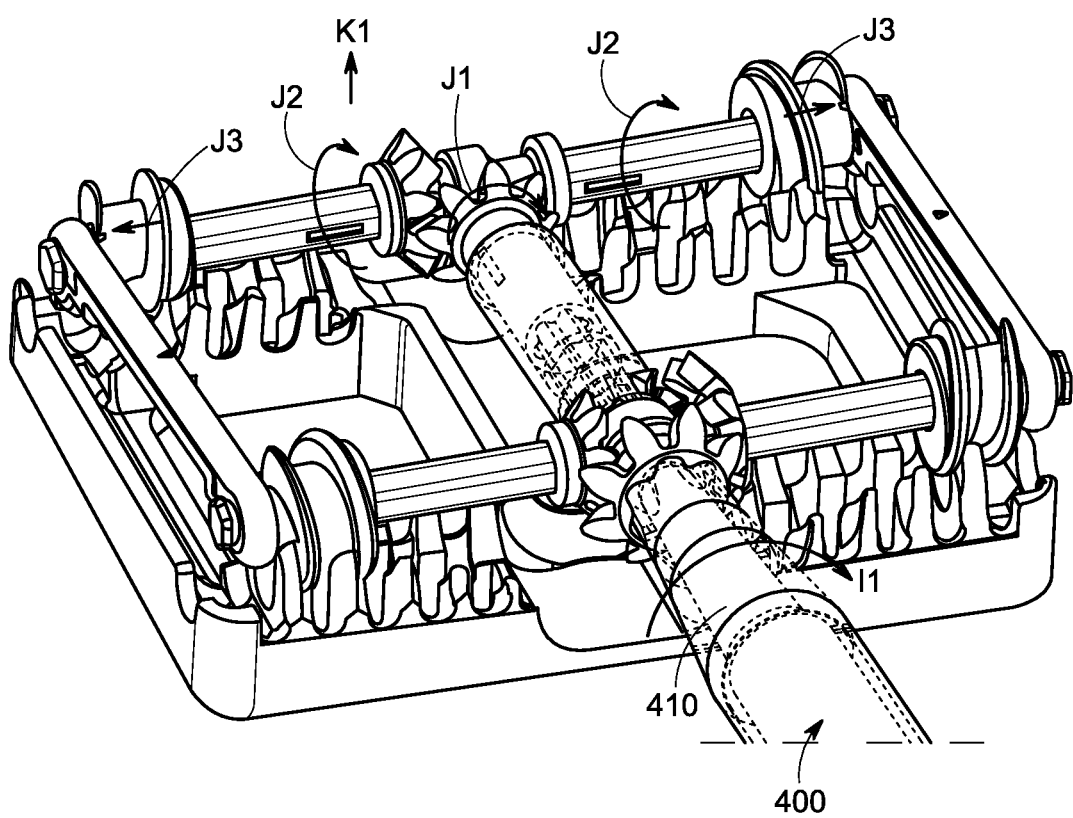
FIG. 6 is a partially exploded view of an example interbody fusion device illustrating independent operation of only the driving gears and axles within the first lateral portion (independent posterior axis adjustment) of the interbody fusion device in turn driving only the translating axle in the first lateral portion of the interbody device creating unequal expansion or a lordosis operating mode.

With reference to FIGS. 6 and 1C, a further lordosis mode, or independent adjustment of the posterior axis of an example interbody fusion device 100 will now be described. In the lordosis mode, the first driving mechanism 200 of the interbody fusion device 100 can be operated independently of the second driving mechanism 250, lordotically adjusting the configuration of the interbody fusion device 100 at the posterior side 104. The posterior side 104 can be expanded to a point above the anterior side 106 resulting in negative lordosis (kyphosis).

To begin with the lordosis mode, the user may extend only the first driver 410 of the surgical instrument 400, allowing only the first driver 410 to engage the driving gear 314 of the first gear assembly 310, as shown in FIG. 3D. In this lordosis mode, the second first driver 420 of the surgical instrument 400 does not engage the first driving gear 354 of the second gear assembly 350. Then, the user may apply torque to in a direction generally perpendicular to the first driving mechanism 200 of the interbody fusion device 100 by turning the first driver 410 e.g. in the clockwise direction, as indicate by arrow 11.

With reference to FIGS. 6 and 1C, the turning the first driver 410 of the surgical instrument 400 causes the driving gear 314 of the first gear assembly 310 to rotate e.g. in the clockwise direction as indicated by arrow J1, which in turn drives the translating gear 312 e.g. in the outward direction as indicated by arrow J2, causing the first axle 202 to rotate e.g. in the outward direction as indicated by arrow J2. The rotation of the first axle 202 causes the screw members 220, 222 to travel on the riser members e.g. in the outward direction as indicated by arrow J3.

The movement of the riser members 220, 222 on the individual riser members causes the first shell member 110 and the second shell member 120 to move linearly relative to each other or expand at the posterior side 104, lordotically adjusting the interbody fusion device 100 at the posterior side 104, as indicated by arrow K1. Completing expansion of the posterior side 104 to a point of adjustment above the anterior side 106 would kyphotically adjust (negative lordosis) the interbody fusion device 100.

It should be noted that while the operations of the driving gear 314 and the translating gear 312 of the first gear assembly 310, and the first driving mechanism 20 are described in sequential steps for clarity, the rotation, translation, or movement of the above assemblies, mechanisms or parts occur simultaneously upon turning of the first driver 410 of the surgical instrument 400. Further, the example shown in FIG. 6 lordotically adjusts the interbody fusion device 100 at the posterior side 104 by turning the first driver 410 of the surgical instrument 400 in the clockwise direction. A reverse operation by turning the first driver 410 e.g. in the counterclockwise direction may adjust the degree of the lordosis of the interbody fusion device 100.

Figure 9A:
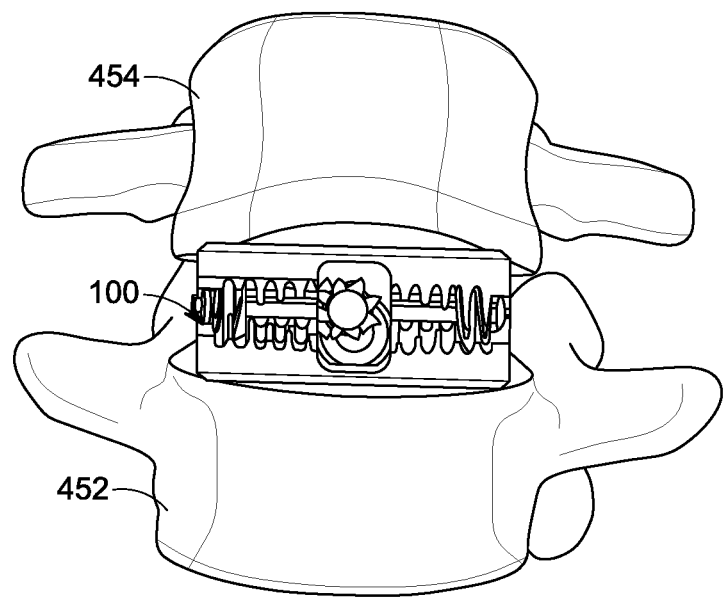
FIGS. 9A-9B depict an example interbody fusion device placed between adjacent vertebrae.
Figure 9B:
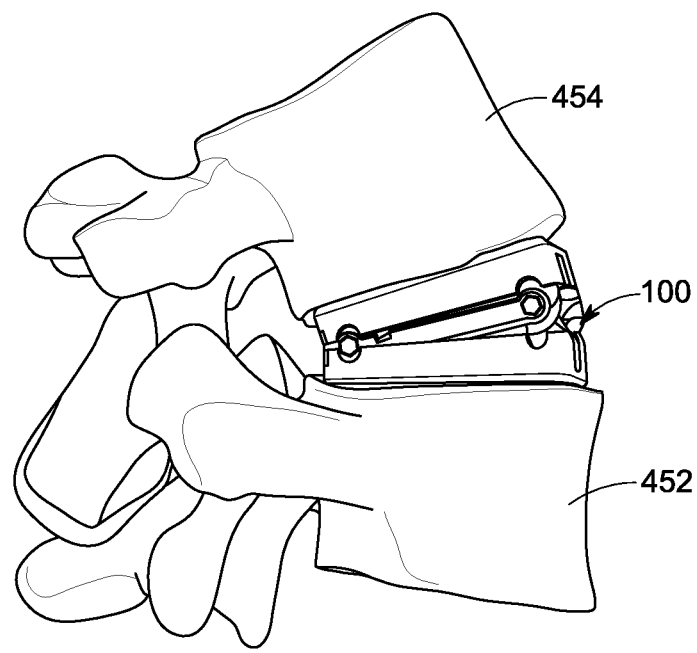

FIGS. 9A-9B show an example interbody fusion device 100 placed in adjacent intervertebral bodies 452, 452, and expanded and/or lordotically adjusted according to embodiments of the disclosure.

With reference now to FIGS. 10A-14C, embodiments of the interbody fusion device 100 may include a fixation assembly 500, which can secure the interbody fusion device 100 in the intervertebral space to prevent unwanted lateral or medial migration of the interbody fusion device 100 and prohibit the interbody fusion device 100 from unwinding or backing down following adjustment.

Figure 10A:
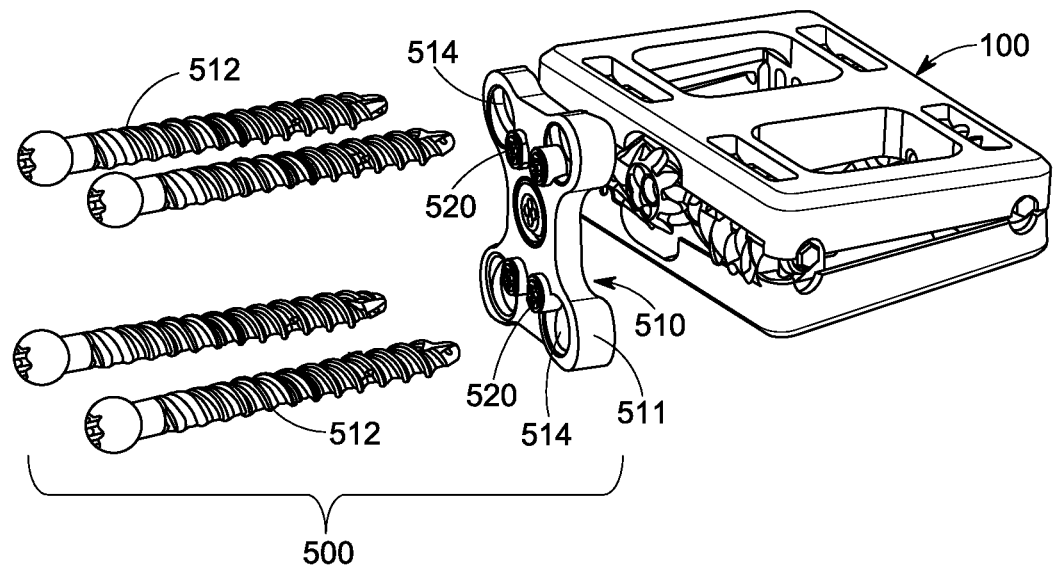
FIGS. 10A-10B depict an example interbody fusion device and a fixation assembly according to embodiments of the disclosure.
Figure 10B:
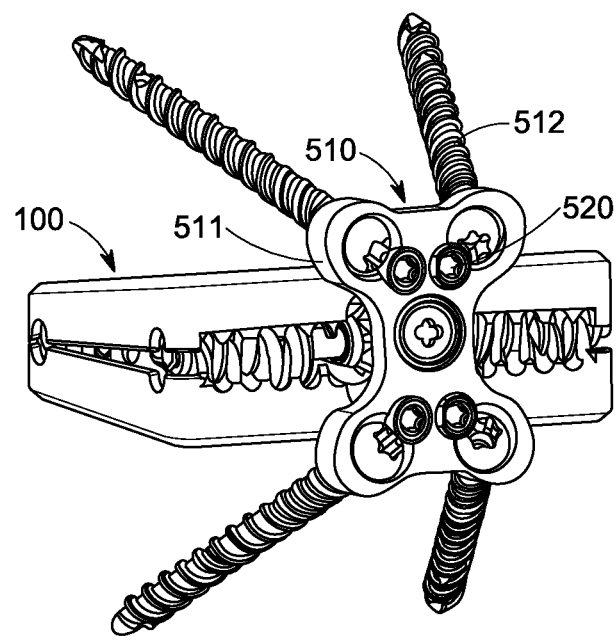
Figure 14A:
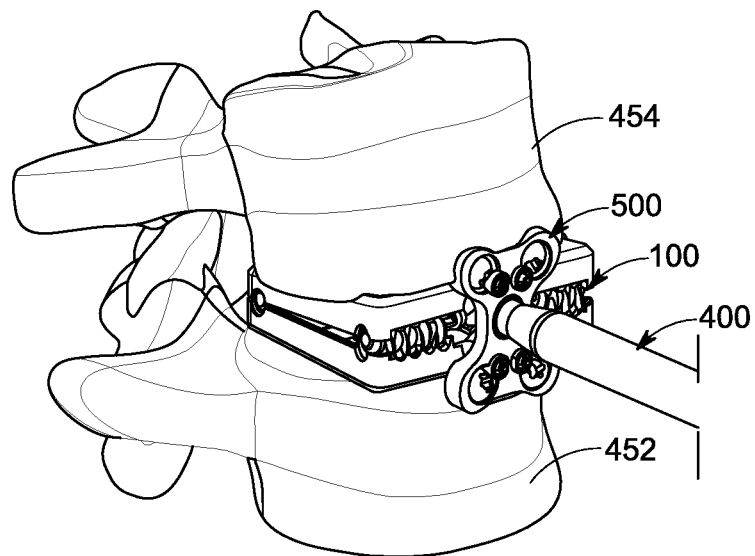
FIGS. 14A-14C illustrate attaching of an example fixation plate to an example interbody fusion device and securing of the interbody fusion device to adjacent vertebrae using a surgical instrument.
Figure 14B:
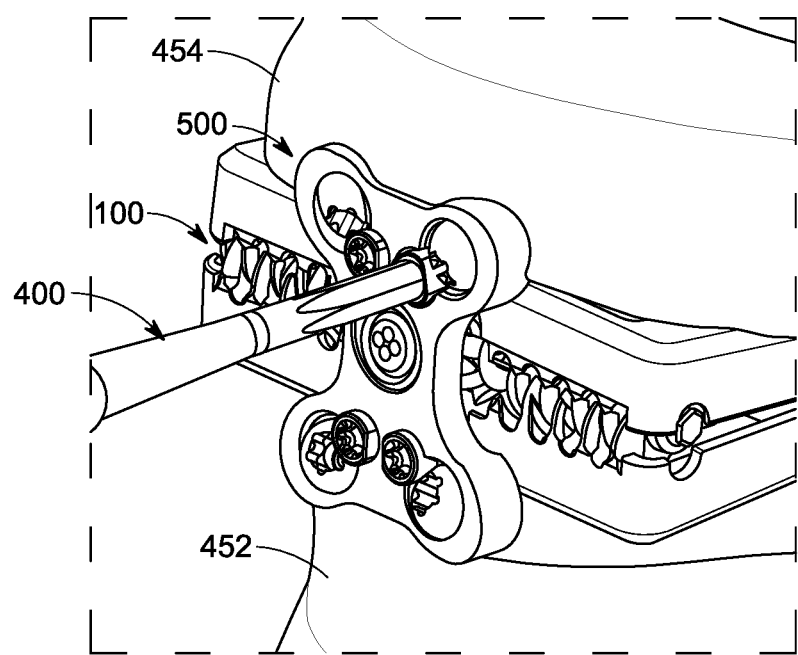

As shown in FIGS. 10A-10B, the fixation assembly 500 in general comprises a plate assembly 510 and fasteners 512. The plate assembly 510 is configured to be attachable to the interbody fusion device 100. The plate assembly 510 comprises a plate member 511 provided with apertures 514 configured for insertion of the fasteners 512 therethrough to secure to an inferior vertebral body and a superior vertebral body respectively. The plate assembly 510 may also include fastener-lock mechanisms 520 to prevent fasteners from backing out of the vertebral bodies. While four apertures 514 in the plate member 511 and four fasteners 512 are shown, other embodiments may include fewer or more than four apertures in the plate member 511. Likewise, while four fastener-lock mechanisms 520 are shown, other embodiments may include fewer or more than four fastener-lock mechanisms. Further, FIG. 10B depicts an assembled view where the plate assembly 510 is attached to the interbody fusion device 100. It should be noted that in use, the plate assembly 510 can be attached to the interbody fusion device 100 in situ, or when the interbody fusion device 100 has been inserted in the patient and placed between adjacent vertebral bodies. FIGS. 14A-14B shows attaching of a plate assembly 510 to an interbody fusion device 100 after the interbody fusion device 100 has been placed, expanded, and/or lordotically adjusted to a proper configuration between adjacent vertebrae. If desired, the plate assembly 510 may also be attached to the interbody fusion device 100 prior to implantation of the interbody fusion device.

In certain embodiments, the plate member 511 may be constructed from a material having sufficient strength such as titanium, stainless steel or other metal or alloy to provide orthotic support or supplemental fixation in addition to preventing migration or unwinding of the interbody fusion device 100. As used herein, the term "supplemental fixation" refers to an embodiment of the fixation plate serving as an orthotic capable of holding adjacent vertebrae in place or immobilizing movement of adjacent vertebrae until arthrodesis (bony fusion) takes place.

Figure 11:
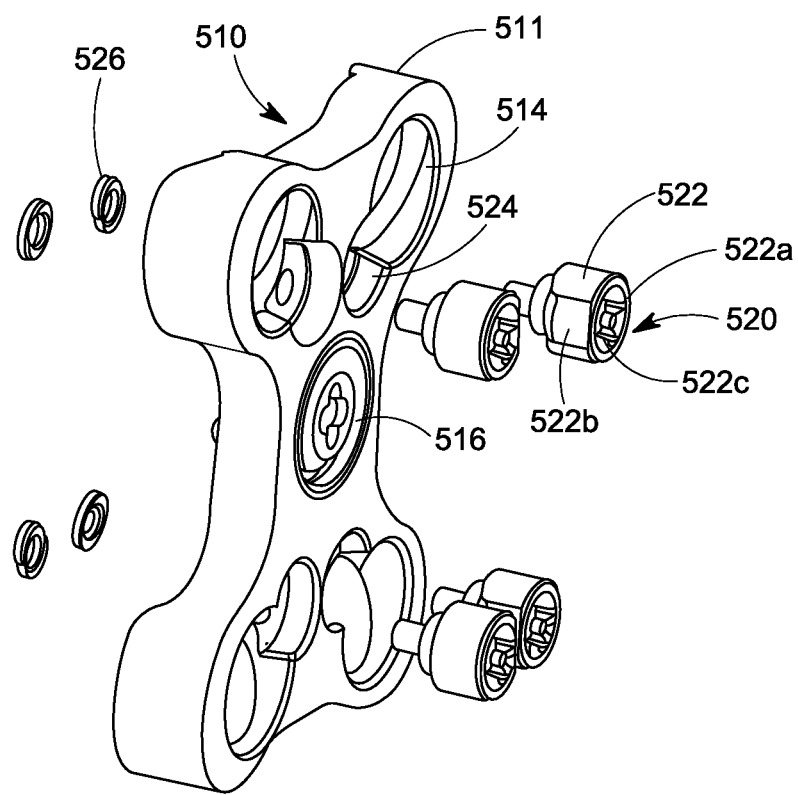
FIG. 11 depicts an example fixation plate according to embodiments of the disclosure.

With reference to FIG. 11, the plate member 511 may generally in an H-beam shape or a bone shape, with cutouts in the sides to minimize or reduce the profile of the plate. For example, the plate member 511 may have a reduced dimension in the middle portion as compared to the upper and lower portions of the plate member 511. The apertures 514 may be provided in the upper and lower portions of the plate member 511. A reduced or optimized profile of the plate assembly 510 allows for improved visualization of the interbody fusion device 100 inside the patient especially e.g. in an anterior view. A reduced profile of the plate assembly 510 also facilitates insertion and placement of the plate assembly 510 in the patient anatomy. Other suitable size and shape of the fixation plate are possible, and the present claims are not so limited. The plate member 511 may include a geometry feature 516 e.g. an annular geometry feature provided with threading for connecting with a surgical instrument.

With reference to FIG. 11, the locations of the apertures 514 in the plate member 511 may be spaced apart as shown to allow the fasteners 512 to be inserted through and directed to an inferior vertebral body and a superior vertebral body respectively. An aperture 514 in the plate member 511 may be angled e.g. at 0-15 degrees with respect to a reference plane perpendicular to a surface of the plate member 511. An angled aperture allows for an angled trajectory of a fastener inserted through the aperture, as better viewed in FIG. 10B, providing for an optimal angle for the fastener to anchor to a vertebral body. Further the plate member 511 may possess a curved or non-parallel profile geometry that exists at the location of the apertures in relation to the middle body section to allow for even further angled trajectory of fasteners above 15 degrees for even more optimal cortical bone purchase. An aperture 514 may include a counterbore or countersink portion configured for receiving the head of the fastener 512. The head of the fasteners 512 may have a spherical shape as shown FIG. 10A or any other suitable shapes such as tapered or cylindrical shape to facilitate or allow for fastener trajectory adjustment. Examples of fasteners include but are not limited to spinal expansion head screws, spinal locking screws, spinal self-locking screws, spinal shaft screws, spinal nails, spinal barbs, spinal hooks, or other threaded or non-threaded members which can be anchored to a vertebral body.

With reference to FIG. 11, the plate assembly 510 may include at least one fastener-lock mechanism 520 configured to prevent a fastener from backing out. In FIG. 11, four fastener-lock mechanisms 520 are provided, each being located adjacent to an aperture 514 in the plate member 511. An example fastener-lock mechanism 520 may include a lock rod 522 received in a recess 524 adjacent to an aperture 514 in the plate member 511, and an adapter 526 welded or attached to an end of the lock rod 522 to retain the lock rod 522 in the recess 524 and allow the lock rod 522 to turn. The head of the lock rod 522 may have a rounded side portion 522a, a flat side portion 522b, and an end 522c provided with a feature such as a female hexalobe to receive a driver for engaging the lock mechanism 520. When the lock rod 522 is turned to set the lock mechanism 520 to an unlocked or open state, the head flat side portion 522b faces the aperture 514 in the plate member 511, leaving the aperture 514 open to allow a fastener 512 to insert through. After the fastener 512 is driven all the way through into a vertebral body and the fastener head received in the countersink of the aperture, the lock rod 522 can be turned to set the lock mechanism 520 in a locked state, where the head rounded side portion 522a extends over at least a portion of the aperture 514 or over the fastener 512, prohibiting the fastener 512 from backing out. The lock mechanism 520 of the disclosure allows quick "one-step" locking, requiring only one turn of the lock rod 522 with a driver to lock or unlock the fastener 512. The use of a "one-step" locking mechanism can also simplify or reduce the profile of the plate assembly 510, which is beneficial for inserting and placing the apparatus in the patient anatomy.

Figure 12A:
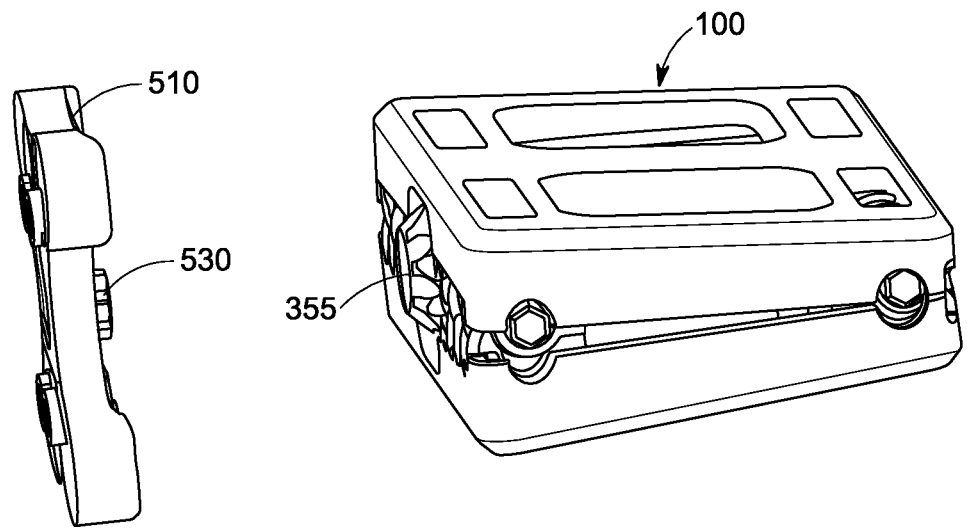
FIGS. 12A-12B depict attachment of an example fixation plate to an example interbody fusion device according to embodiments of the disclosure.
Figure 12B:
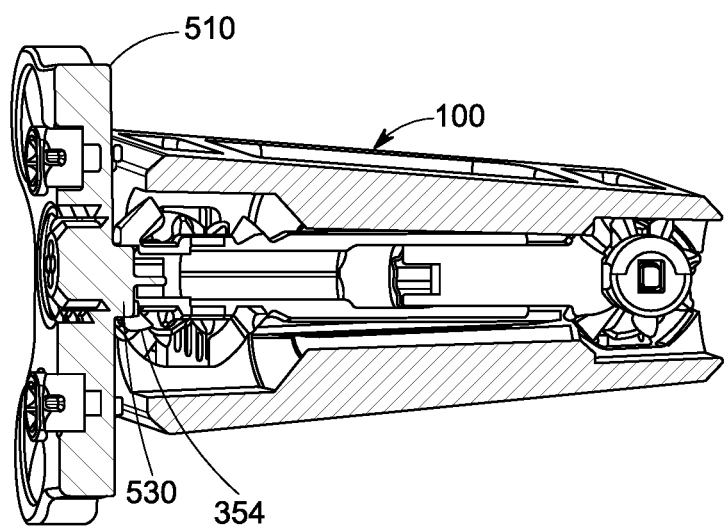
Figure 13A:
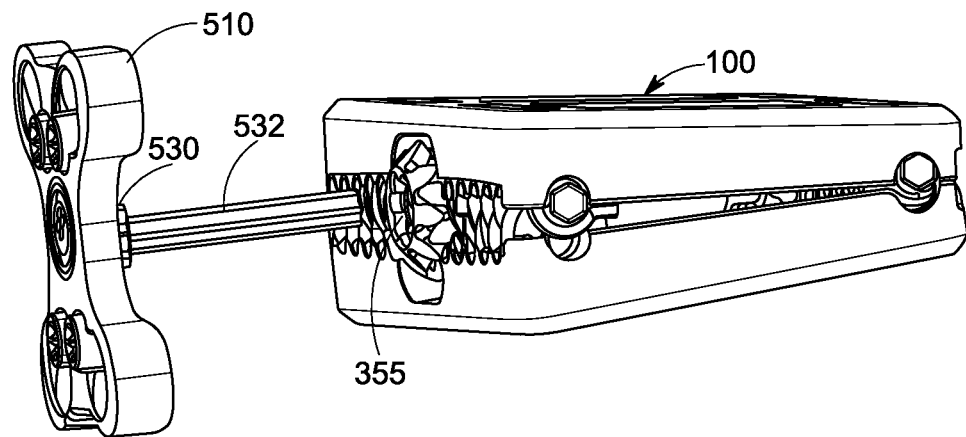
FIGS. 13A-13B depict attachment of another example fixation plate to an example interbody fusion device according to embodiments of the disclosure.
Figure 13B:
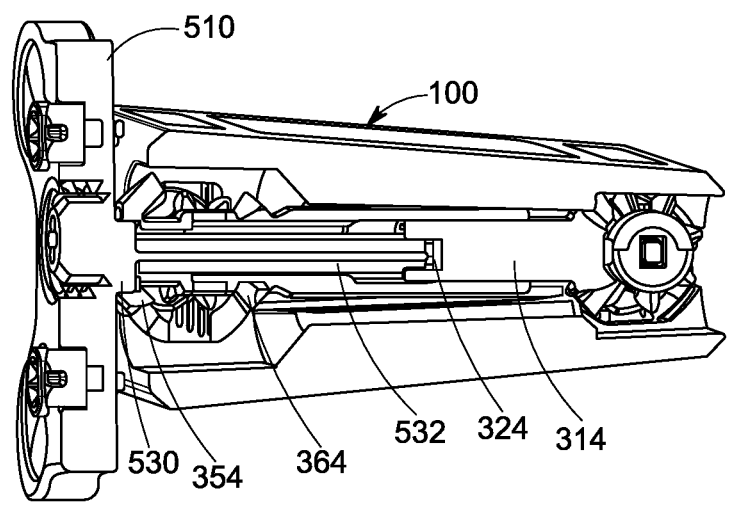

With reference to FIGS. 12A-12B and 13A-13B, the plate assembly 510 may include a geometry feature or features configured for attachment to the interbody fusion device 100. The plate assembly 510 may include a male geometry feature extended from the plate member configured to be inserted into a female geometry feature in a driving gear of the first gear assembly 310 and/or the second gear assembly 350. FIGS. 12A-12B show a plate assembly 510 including a male geometry 530 e.g. a male hexalobe configured to be tightly mated into the female hexalobe 355 in the first driving gear 354 of the second gear assembly 350. Once the plate assembly 510 is inserted into the interbody fusion device 100 and fastened to the vertebral bodies, the male hexalobe 530 of the plate assembly 510 can prevent unwanted rotation of the first driving gear 354 of the second gear assembly 350, serving as a secondary lock to prevent unwinding or backing down following adjustment of the interbody fusion device 100. FIGS. 13A-13B show a plate assembly 510 including an elongate male geometry 532 e.g. a male hexalobe configured to pass through the first driving gear 354 and the second driving gear 364 of the second gear assembly 350, and be tightly mated into the female hexalobe 324 in the driving gear 314 of the first gear assembly 310. Once the plate assembly 510 is inserted into the interbody fusion device 100 and fastened to the vertebral bodies, the elongate male hexalobe 532 prevents unwanted rotation of the driving gear 314 of the first gear assembly 310, serving as a secondary lock to prevent unwinding or backing down following adjustment of the interbody fusion device 100. In certain embodiments of the disclosure, the plate assembly 510 may include a first male geometry configured to be tightly mated into the female geometry in the driving gear 314 of the first gear assembly 310, and a second male geometry configured to be tightly mated into the female geometry in the first driving gear 354 of the second gear assembly 350. For example as shown in FIG. 13B, the plate assembly 510 may include a first male geometry 532 e.g. an elongate male hexalobe configured to be tightly mated into the female hexalobe 324 in the driving gear 314 of the first gear assembly 310, and a second male geometry 530 e.g. a male hexalobe configured to be tightly mated into the female hexalobe 355 in the first driving gear 354 of the second gear assembly 350.

U.S. Application Ser. No. 16/993,265 entitled "Dual Axis Adjustable Spinal Systems and Interbody Fusion Devices with Fixation" filed concurrently with this application, describes various embodiments of fixation assemblies for interbody fusion devices and spinal systems, the disclosure of all of which is incorporated herein by reference in its entirety.

Figure 14C:
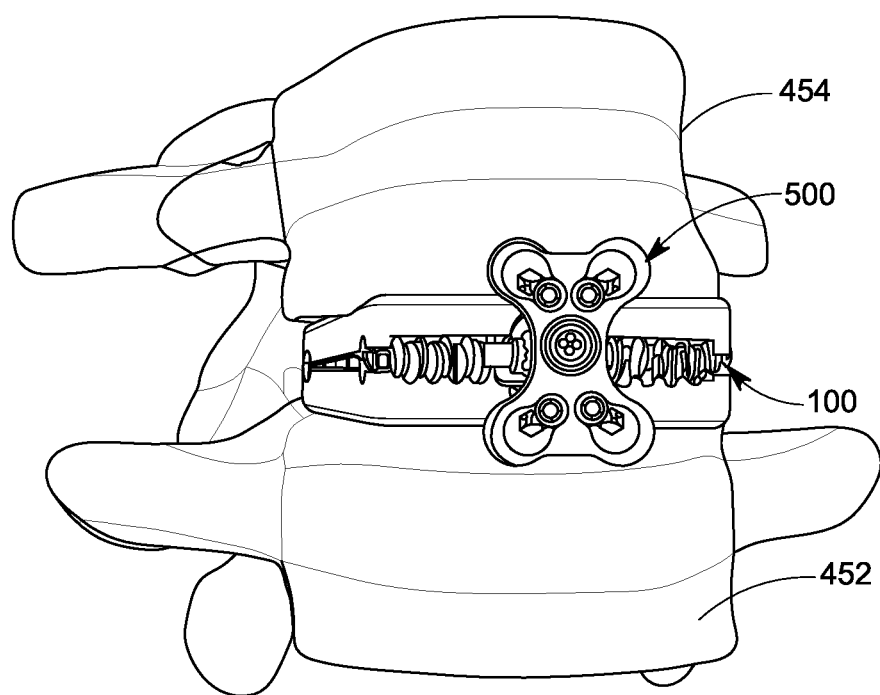

With reference to FIGS. 14A-14C, in use, the plate assembly 510 can be inserted and attached to an interbody fusion device 100 in situ. For instance, an interbody fusion device 100 in a contracted configuration can be first inserted and placed between adjacent vertebrae 452, 454 via an anterior lumbar interbody fusion (ALIF) procedure, or any other suitable surgical procedures. The interbody fusion device 100 can be expanded and/or lordotically adjusted using a surgical instrument 400, forming a suitable configuration between the adjacent vertebrae 452, 454, as described above in conjunction with FIGS. 3-6.

Then, the plate assembly 510 can be introduced to the target area, via the same surgical approach for inserting and placing the interbody fusion device 100, and attached to the interbody fusion device 100. According to embodiments of the disclosure, the surgical instrument 400 used for placing and operating the interbody fusion device 100 can be used for inserting and attaching the plate assembly 510. By way of example, the surgeon can connect the plate assembly 510 to the surgical instrument 400 via the thread on the annular geometry feature 516 in the plate member 511, introduce the plate assembly 510 to the target area via the same surgical approach, and insert the plate assembly 510 to the interbody fusion device 100, as shown in FIG. 14A.

Fasteners 512 e.g. spinal screws can be then inserted through the apertures 514 in the plate member 511 and screwed into an inferior vertebral body 452 and a superior vertebral body 454 respectively. Once the fasteners 512 are driven all the way, the fastener-lock mechanisms 520 of the plate assembly 510 can be actuated using the surgical instrument 400 to lock the fasteners 512 to prevent them from backing out, as shown in FIG. 14B. The interbody fusion device 100 can be then prevented from unwanted lateral or medial migration and unwinding or backing down following expansion or lordotic adjustment, as shown in FIG. 14C.

Embodiments of an interbody fusion device are described in conjunction with FIGS. 1A-14C. Beneficially, embodiments of the interbody fusion device of the disclosure allow the surgeon to apply torque from the anterior direction perpendicularly that is then translated to that of the driving mechanisms responsible for expansion and lordotic adjustment of the interbody fusion device. The dual-axis driving mechanisms allows the surgeon to adjust the height and unique level of lordosis to achieve complete anatomical personalization for the patient. For example, embodiments of the interbody fusion device of the disclosure allows the surgeon to set the interbody fusion device in fine configurations, to any unique height (e.g. 11.6 mm) and/or unique angle (e.g. 21.7°) needed for the patient's spinal balance profile. Conventional techniques may have implants built at only a few predetermined lordotic configurations such as 20°, 25°, 30°.

The interbody fusion device can provide increased surgical efficiency. Conventionally, surgeons must perform impactful trialing, or sizing of the implant to determine the size of an implant needed for a specific patient. According to embodiments of the disclosure, the interbody fusion device can start at a smaller contracted height and then increase in height. This allows for streamlining or drastically reducing the trialing process, which can in turn decrease the barbaric and rough impact associated with the trialing process. The mechanism of the implant also has enough space to distract the vertebral bodies back to their normal desired positions. This control of distraction also takes out the need to distract using an extra instrument.

The use of a fixation assembly prevents the interbody fusion device from unwanted lateral or medial migration and unwinding or backing down following expansion or lordotic adjustment. The fixation plate can be constructed with sufficient strength to provide orthotic support or supplemental fixation. The fixation plate is implantable and configurable to attach to the interbody fusion device via a single surgical approach and patient position, thereby minimizing disruption to the patient anatomy. The geometry such as the male geometries in the fixation plate can act as secondary safety locks for the interbody fusion device, preventing the interbody fusion device from unwinding or backing down following adjustment.

The interbody fusion device also provides benefits pertaining manufacturing and hospital administration. It can reduce inventory. Currently an implant size must exist for every height, usually in 1 mm degree increments, along with 5-degree increments of lordosis. This quickly makes the number of implants needed on hand very great. The interbody fusion device according to embodiments of the disclosure is fully adjustable, which ultimately cuts down on the number of implants needed in the operating room or needed to be held in in inventory.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "first" or "second" is used to distinguish one element from another in describing various similar elements and should not be construed as in any particular order unless the context clearly dictates otherwise.

Those skilled in the art will appreciate that various other modifications may be made. All these or other variations and modifications are contemplated by the inventors and within the scope of the invention.

The invention claimed is:

1. An interbody fusion device, comprising:
a housing comprising a first shell member and a second shell member, at least the first shell member comprises a plurality of riser members;
a driving mechanism operable to expand and/or contract the housing, the driving mechanism comprising an axle having a longitudinal axis and a screw member having a through-opening adapted to allow the axle to pass;
a gear assembly operable to transfer torque to the driving mechanism, the gear assembly comprising a first translating gear coupled to the axle and a first driving gear configured to receive torque applied from a direction non-parallel to the longitudinal axis of the axle and drive the first translating gear, whereby application of torque to the first driving gear causes the first translating gear and the axle to rotate about the longitudinal axis, causing the screw member to rotate with and travel along the axle, wherein the screw member is engageable with the plurality of riser members, whereby rotation of the screw member causes the first shell member and the second shell member to move relative to each other to effect expansion and/or contraction of the housing.

2. The interbody fusion device of claim 1, wherein the first driving gear of the gear assembly is configured to receive torque applied from the direction generally perpendicular to the longitudinal axis of the axle.

3. The interbody fusion device of claim 2, wherein
the screw member comprises a first screw member and a second screw member, the first screw member and the second screw member each having a through-opening adapted to allow the axle to pass;
the plurality of riser members are configured for receiving the first screw member and the second screw member;
the axle is engageable with the first screw member and the second screw member, whereby rotation of the axle about the longitudinal axis causes the first screw member and the second screw member to rotate with and travel along the axle; and
the first screw member and the second screw member are engageable with the plurality of riser members, whereby rotation of the first screw member and the second screw member causes the first shell member and the second shell member to move relative to each other to effect expansion and/or contraction of the housing.

4. The interbody fusion device of claim 3, wherein the first screw member is disposed at a first lateral side of the first translating gear, the second screw member is disposed at a second lateral side of the first translating gear, and the first screw member and the second screw member are configured to travel in opposition directions upon rotation of the axle.

5. The interbody fusion device of claim 1, wherein
the axle comprises a first section and a second section, the first section and the second section of the axle being rotatably connected to a connection member, the first translating gear being coupled to the first section of the axle, and
the gear assembly further comprises a second translating gear coupled to the second section of the axle, and a second driving gear configured to receive torque applied from the direction non-parallel to the longitudinal axis of the axle and drive the second translating gear, whereby application of torque to the second driving gear causes the second translating gear and the second section of the axle to rotate about the longitudinal axis.

6. The interbody fusion device of claim 5, wherein the first driving gear and the second driving gear of the gear assembly are configured to receive torque applied from the direction generally perpendicular to the longitudinal axis of the axle.

7. The interbody fusion device of claim 5, wherein the first driving gear has a first pitch and the second driving gear has a second pitch different from the first pitch.

8. The interbody fusion device of claim 5, wherein the first driving gear and the second driving gear are connected via a tubular section and operate as a single unit.

9. The interbody fusion device of claim 8, wherein the connection member connecting the first section and the second section of the axle comprises a ring structure configured to receive the tubular section and allow the first driving gear and the second driving gear to rotate.

10. The interbody fusion device of claim 5, wherein
the screw member comprises a first screw member and a second screw member, the first screw member having a through-opening adapted to allow the first section of the axle to pass, the second screw member having a through-opening adapted to allow the second section of the axle to pass;
the plurality of riser members are configured for receiving the first screw member and the second screw member;
the first section of the axle is engageable with the first screw member, whereby rotation of the first section of the axle about the longitudinal axis causes the first screw member to rotate with and travel along the first section of the axle, the second section of the axle is engageable with the second screw member, whereby rotation of the second section of the axle about the longitudinal axis causes the second screw member to rotate with and travel along the second section of the axle; and
the first screw member and the second screw member are engageable with the plurality of riser members, whereby rotation of the first screw member and the second screw member causes the first shell member and the second shell member to move relative to each other to effect expansion and/or contraction of the housing.

11. An interbody fusion device, comprising:
a housing comprising a first shell member and a second shell member;
a first driving mechanism arranged in the housing at a first lateral area, a second driving mechanism arranged in the housing at a second lateral area, the first driving mechanism comprising a first axle having a longitudinal axis, and the second driving mechanism comprising a second axle having a longitudinal axis;
a first gear assembly operable to transmit torque to the first driving mechanism, the first gear assembly comprising a translating gear coupled to the first axle and a driving gear configured to receive torque applied from a direction non-parallel to the longitudinal axis of the first axle and drive the translating gear, whereby application of torque to the driving gear causes the translating gear and the first axle to rotate about the longitudinal axis of the first axle, thereby actuating the first driving mechanism to effect expansion and/or contraction of the housing at the first lateral area; and
a second gear assembly operable to transmit torque to the second driving mechanism, the second gear assembly comprising at least a first translating gear coupled to the second axle and a first driving gear configured to receive torque applied from a direction non-parallel to the longitudinal axis of the second axle and drive the first translating gear, whereby application of torque to the first driving gear causes the first translating gear and the second axle to rotate about the longitudinal axis of the second axle, thereby actuating the second driving mechanism to effect expansion and/or contraction of the housing at the second lateral area, wherein
the first gear assembly is operable independently of the second gear assembly, whereby a degree of expansion and/or contraction of the housing at the first lateral area is independently adjustable, and/or
the second gear assembly is operable independently of the first gear assembly, whereby a degree of expansion and/or contraction of the housing at the second lateral area is independently adjustable.

12. The interbody fusion device of claim 11, wherein the driving gear of the first gear assembly is configured to receive torque applied from the direction generally perpendicular to the longitudinal axis of the first axle, and the first driving gear of the second gear assembly is configured to receive torque applied from the direction generally perpendicular to the longitudinal axis of the second axle.

13. The interbody fusion device of claim 11, wherein the first gear assembly and the second gear assembly are simultaneously operable, whereby a degree of expansion and/or contraction of the housing at the first lateral area and a degree of expansion and/or contraction of the housing at the second lateral area are simultaneously adjustable.

14. The interbody fusion device of claim 11, wherein
the second axle comprises a first section and a second section, the first section and the second section each being rotatably connected to a connection member, the first translating gear of the second gear assembly is coupled to the first section;
the second gear assembly further comprises a second translating gear coupled to the second section, and a second driving gear configured to receive torque applied from the direction non-parallel to the longitudinal axis of the second axle and drive the second translating gear, whereby application of torque to the second driving gear causes the second translating gear and the second section of the second axle to rotate about the longitudinal axis of the second axle.

15. The interbody fusion device of claim 14, wherein the first driving gear and the second driving gear of the second gear assembly are operable as a single unit.

16. The interbody fusion device of claim 15, wherein
the first driving gear and the second driving gear of the second gear assembly are coupled to form a tubular section; and
the connection member rotatably connecting the first section and the second section of the second axle comprises a ring structure configured to receive the tubular section allowing the first driving gear and the second driving gear to rotate.

17. The interbody fusion device of claim 15, wherein
the driving gear of the first gear assembly comprises an elongate portion, the second driving gear of the second gear assembly comprises a sleeve section, the elongate portion of the driving gear of the first gear assembly being rotatably received in the sleeve section of the second driving gear of the second gear assembly, and
the elongate portion of the driving gear of the first gear assembly comprises an end having a feature for engaging with a first driver of a surgical instrument, and the first driving gear of the second gear assembly comprises a feature for engaging with a second driver in the surgical instrument, thereby allowing the surgical instrument to operate the first gear assembly and the second gear assembly simultaneously, or to operate the first gear assembly independently of the second gear assembly, or to operate the second gear assembly independently of the first gear assembly.

18. The interbody fusion device of claim 14, wherein
the first driving mechanism comprises a first screw member and a second screw member, the first screw member and the second screw member of the first driving mechanism each having a through-opening adapted to allow the first axle to pass;
the second driving mechanism comprises a first screw member and a second screw member, the first screw member of the second driving mechanism having a through-opening adapted to allow the first section of the second axle to pass, the second screw member of the second driving mechanism having a through-opening adapted to allow the second section of the second axle to pass;
at least the first shell member comprises a plurality of riser members for receiving the first screw member and the second screw member of the first driving mechanism and the first screw member and the second screw member of the second driving mechanism;
the first axle of the first driving mechanism is engageable with the first screw member and the second screw member of the first driving mechanism, whereby rotation of the first axle of the first driving mechanism causes the first screw member and the second screw member of the first driving mechanism to rotate with and travel along the first axle of the first driving mechanism, causing the first shell member and the second shell member to move relative to each other to effect expansion and/or contraction of the housing at the first lateral area; and
the first section of the second axle is engageable with the first screw member of the second driving mechanism, the second section of the second axle is engageable with the second screw member of the second driving mechanism, whereby rotation of the first section and the second section of the second axle causes the first screw member and the second screw member of the second driving mechanism to rotate with and travel along the first section and the second section of the second axle respectively, causing the first shell member and the second shell member to move relative to each other to effect expansion and/or contraction of the housing at the second lateral area.

19. The interbody fusion device of claim 11, further comprising a fixation assembly for securing the interbody fusion device in adjacent vertebral bodies, the fixation assembly comprising a plate assembly, at least one first fastener and at least one second fastener, wherein the plate assembly is configured to be attachable to the interbody fusion device and comprises a plate member provided with at least one first aperture for insertion of the at least one first fastener therethrough to a first vertebral body and at least one second aperture for insertion of the at least one second fastener therethrough to a second vertebral body, thereby allowing the plate assembly to be attached to the interbody fusion device in situ and secured to the first and second vertebral bodies.

20. The interbody fusion device of claim 19, wherein the plate member comprises a first geometry feature configured to mate a geometry feature in the driving gear of the first gear assembly to prevent rotation of the driving gear of the first gear assembly relative to the plate member.

21. The interbody fusion device of claim 20, wherein the plate member further comprises a second geometry feature configured to mate a geometry feature in the first driving gear of the second gear assembly to prevent rotation of the first driving gear of the second gear assembly relative to the plate member.

22. The interbody fusion device of claim 21, wherein the plate member is constructed from a material having strength capable of providing supplemental fixation of the first and second vertebral bodies.

23. The interbody fusion device of claim 21, wherein the plate assembly comprises a first fastener-lock mechanism configured to prohibit the at least one first fastener from backing out of the at least one first aperture, and a second fastener-lock mechanism configured to prohibit the at least one second fastener from backing out of the second aperture.

24. An interbody fusion device, comprising:
a housing comprising a first shell member and a second shell member;
a first driving mechanism arranged in the housing at a first lateral area, a second driving mechanism arranged in the housing at a second lateral area, the first driving mechanism comprising a first axle having a longitudinal axis, and the second driving mechanism comprising a second axle having a longitudinal axis;
a first gear assembly operable to transmit torque to the first driving mechanism, the first gear assembly comprising a translating gear coupled to the first axle and a driving gear configured to receive torque applied from a direction non-parallel to the longitudinal axis of the first axle and drive the translating gear, whereby application of torque to the driving gear causes the translating gear and the first axle to rotate about the longitudinal axis of the first axle, thereby actuating the first driving mechanism to effect expansion and/or contraction of the housing at the first lateral area; and
a second gear assembly operable to transmit torque to the second driving mechanism, the second gear assembly comprising at least a first translating gear coupled to the second axle and a first driving gear configured to receive torque applied from a direction non-parallel to the longitudinal axis of the second axle and drive the first translating gear, whereby application of torque to the first driving gear causes the first translating gear and the second axle to rotate about the longitudinal axis of the second axle, thereby actuating the second driving mechanism to effect expansion and/or contraction of the housing at the second lateral area, further comprising
a first thrust bearing coupling the first axle and the second axle at a first end of the first axle and a first end of the second axle;
a second thrust bearing coupling the first axle and the second axle at a second end of the first axle and a second end of the second axle, wherein
the first thrust bearing and the second thrust bearing are configured to allow the first axle and the second axle to rotate about the longitudinal axis of the first axle and the second axle respectively, and prohibit translational movement of the first axle and the second axle respectively.

* * * * *